US006444444B1

(12) United States Patent
Anand et al.

(10) Patent No.: US 6,444,444 B1
(45) Date of Patent: Sep. 3, 2002

(54) GENES ENCODING MYCOBACTERIAL PROTEINS ASSOCIATED WITH CELL BINDING AND CELL ENTRY AND USES THEREOF

(75) Inventors: Naveen N. Anand, Downsview; Michel H. Klein, Willowdale, both of (CA)

(73) Assignee: Aventis Pasteur Limited, Toronto (CA)

( * ) Notice: Subject to any disclaimer, the term of this patent is extended or adjusted under 35 U.S.C. 154(b) by 0 days.

(21) Appl. No.: 08/677,970

(22) Filed: Jul. 10, 1996

(51) Int. Cl.[7] .................... C12P 21/06; C12N 15/09; C12N 15/00; C07H 21/04
(52) U.S. Cl. .................... 435/69.3; 435/70.1; 435/71.1; 435/71.2; 435/252.3; 435/254.11; 435/320.1; 435/325; 514/44; 536/23.7; 935/9; 935/11; 935/12; 935/22; 935/52; 935/66
(58) Field of Search ................ 435/69.3, 320.1, 435/70.1, 71.1, 71.2, 325, 252.3, 254.11; 530/350; 536/23.7; 514/44; 935/9, 11, 12, 22, 52, 66

(56) References Cited

U.S. PATENT DOCUMENTS

| 5,580,859 A | * | 12/1996 | Felgner et al. |
| 5,589,466 A | * | 12/1996 | Felgner et al. |
| 5,593,972 A | * | 1/1997 | Weiner et al. |
| 5,620,896 A | * | 4/1997 | Herrmann et al. |
| 6,008,201 A | | 12/1999 | Riley |
| 6,072,048 A | | 6/2000 | Riley |

FOREIGN PATENT DOCUMENTS

| WO | WO 95/17511 | 6/1995 |
| WO | WO 96 26275 | 8/1996 |

OTHER PUBLICATIONS

Philipp et al. PNAS 93:3132–37 4/96.*
Arrudo et al. Science 261: 1454 9/93.*
Abou–Zeid et al Infect. Immun. 59(8):2712–18 8/91.*
Lewin, B. in "Genes IV". Cell press, Cambridge. p. 810, 1990.*
Davis et al. "Microbiology "Harper and Rouv. 1980.*
Lazar et al. Mol. Cell Biology 8(3):1247–52 Mar. 1988.*
Burgess et al. J. Cell Biol. 111:2129–38 Nov. 1990.*
Ellis, R.W., see Chapter 29 of "Vaccines" PLotkin et al. (ed)., published by WB Saunders Company (Philadelphia), see p. 571, 2nd full paragraph, 1988.*
Grange, J.M..; Gibson J; Osborn, T.W.; Collins, C.H. and Yates, M.D. (1983), Tubercle 64: 129–139.
Arruda, S., Bonfim, G.; Huma–Byron, T. and Riley L.W. (1993), Science 261: 1454–1457.
O'Hagan, (1992), Clin. Pharmokinet. 22:1.
Ulmer et al (1993) Curr. Opinion Invest. Drugs 2(9) 983–989.
"Molecular Cloning: A Laboratory Manual" ed Sambrook. J.; Fritsch, E.F. and Maniatis, T. (1989) Cold Spring Harbour Laboratory Press.
Thole, J.E.R. et al (1992) Molecular Microbiology 6(2) 153–163.
Abou–Zeid (1988) Infection and Immunity p. 3046–3051.
Abou–Zeid (1991) Infection and Immunity p. 2712–2718.

* cited by examiner

*Primary Examiner*—Patricia A. Duffy
(74) *Attorney, Agent, or Firm*—Sim & McBurney

(57) ABSTRACT

A gene from a strain of Mycobacterium encoding a protein of molecular weight between about 45 to about 60 kDa and associated with cell binding and cell entry was cloned. The genes and encoded protein have utility in immunogenic preparations or diagnostic applications.

10 Claims, 55 Drawing Sheets

0.8% Agarose Gel

Autoradiograph of Southern Blot 1. marker 1Kb
2. EcoR I digested
3. Hind III digested
4. Nde I digested
5. Bgl II digested
6. Dra III digested
7. Sac I digested
8. Sal I digested
9. Xho I digested
10. Undigested BCG DNA

FIG.4A

DNA SEQUENCE ENCODING MCEP OF BCG

```
ATCGTGGACG CTCTGCCCCG CAACCCCGCG GGGAAGGTGC TCAAGACTGA ACTGCGATTG
CGCTACGGCG CCTGTGTGAA TGTTGAAAGA CGTTCTGCAT CAGCTGGTTT CACGGAGAGA
AGGGAAAATC GACAGAAATT GTAACGTTTG CCCGCTATTG ACGAAGGGTT AAATGTGCGG
ATGCCTTACA CTCCTGGCTG GCCATCGGGT AGATTCCTGT GGTCTCCGTT ACTCCCTGTG
AGTAACGAGG TGGCGGTCAC ACACCAAGGG TCGGGGCAAG GAAGAAGCGT GCGACATGAT
GCGCCGCGGC GCCGCGATAC CCAGGTCGGC GGCTTGAGGG AGCCGCGGTG ACGACGTCGA
CAACGCTTGG CGGTTACGTC CGCGACCAAC TGCAAACCCC GCTGACCCTC GTCGGTGGAT
TCTTTCGCAT GTGTGTGCTG ACTGGAAAGG CGCTGTTTCG CTGGCCGTTC CAGTGGCGCG
AGTTCATTCT GCAGTGCTGG TTCATCATGC GGGTCGGATT TTTACCGACG ATCATGGTCT
CGATACCGCT GACGGTGCTG TTGATCTTCA CGCTCAATAT TCTGCTGGCC CAGTTCGGCG
CGGCAGACAT CTCCGGTTCC GGCGCGGCGA TCGGCGCGGT CACCCAGCTT GGCCCGCTGA
CAACGGTGCT GGTGGTCGCC GGCGCCGGAT CCACGGCCAT CTGCGCCGAC CTGGGTGCCC
GCACCATCCG CGAGGAAATC GACGCGATGG AGGTGCTGGG CATCGATCCC ATCCACCGTC
```

FIG.4B

| | | | | | |
|---|---|---|---|---|---|
| TGGTGGTGCC | GCGGGTGCTC | GCCTCGATGC | TGGTCGCCAC | GCTGCTCAAC | GGCTTGGTGA |
| TCACCGTCGG | CCTGGTCGGT | GGCTTTCTCT | TCGGTGTCTA | TCTGCAGAAC | GTTTCGGGCG |
| GCGCCTACCT | TGCCACGCTG | ACCTTGATCA | CCGGCCTGCC | CGAGGTGGTC | ATCGCAACCA |
| TCAAAGCCGC | AACGTTCGGC | CTGATCGCGG | GCCTTGTCGG | CTGCTATCGG | GGGCTGACCG |
| TCCGTGGCGG | TTCCAAGGGT | CTTGGCACCG | CCGTCAACGA | GACCGTGGTG | CTGTGTGTGA |
| TTGCCCTGTT | CGCCGTCAAC | GTGATCTTGA | CGACCATCGG | TGTGCGATTC | GGGACGGGGC |
| GCTGACATGT | CGACCGCTGC | TGTGCTGCGC | GCCCGCTTCC | CGGGGGCGGT | CGCCAACCTT |
| CGTCAATATG | GAGGTGCCGG | GGCCCGTGGA | TTGGACGAGG | CCGGCCAGCT | CACCTGGTTC |
| GCTTTGACCA | GCATCGGGCA | GATCGCGCAC | GCGCTGCGCT | ACTACCGCAA | GGAGACGCTG |
| CGGCTGATCG | CCCAGATCGG | CATGGGTACC | GGCGCGATGG | CCGTCGTCGG | CGGCACGGTC |
| GCCATCGTTG | GCTTTGTCAC | GCTGTCCGGC | AGCTCGCTGG | TCGCAATCCA | GGGCTTCGCG |
| TCGCTGGGCA | ACATCGGTGT | CGAGGCGTTC | ACCGGGTTCT | TCGCCGCACT | GATCAACGTG |
| CGCATCGCCG | GCCCAGTTGT | CACGGGTGTC | GCCCTGGCGG | CCACGGTCGG | TGCGGGTGCT |

FIG.4C

```
       ACGGCCCGAGC TGGGCGCGAT GCGGATCAGC GAGGAGATCG ATGCCCTGGA AGTGATGGGC
       ATAAAGTCGA TCTCGTTTCT GGCCTCCACC CGGATCATGG CCGGGCTGGT GGTGATCATC
       CCGCTGTACG CGTTGGCGAT CGTTATGTCG TTCCTGTCCC CGCAGATCAC CACCACGGTG
       CTCTACGGGC AGTCGAACGG CACCCTACGAG CATTACTTTC AAACGTTCCT GCGTCCCGAC
1802  GATGCTTTT GGTCCTTCTT GGAGGCCCTC ATCATCACTG CGATCGTCAT GGTCAGCCAC
       TGCTACTACG GGTACGCCGC CGGTGGAGGC CCCGTCGGTG TCGGCGAGGC CGTCGGCCGA
       TCGGATGCGTT TCTCGTTGGT CTCGGTGCAG GTCGTTGTCC TGTTTGCAGC GTTGGCGCTC
       TACGGTGTCG ACCCGAACTT CAATCTCACG GTGTAGCCGC ATGACGACGC CGGGGAAGCT
       GAACAAGGCG CGATGCCGC CCTACAAGAC GGCGGGGTTG GGTCTAGTGC TGGTCTTCGC
       GCTCGTAGTT GCCTTGGTAT ACCTGCAGTT CGGGTTTGGT GATGGATCCC TTCACGCCCA AGACGCAGTT
       GACGATGCTG TCCGCTCGTG CGGGTTTGGT GATGGATCCC GGGTCGAAGG TCACCTATAA
       CGGGGTGGAG ATCGGGCGGG TAGACACCAT CTCGGAGGTC ACACGTGACG GCGAGTCGGC
       GGCCAAGTTC ATCTTGGATG TGGATCCGCG TTACATCCAC CTGATTCCGG CAAATGTGAA  2336
```

FIG. 4D

```
CGCCGACATC AAGGCGACCA CGGTGTTCGG CGGTAAGTAT GTGTCGTTGA CCACGCCGAA
AAACCCGACA AAGAGGCGGA TAACGCCAAA AGACGTCATC GACGTACGGT CGGTGACCAC
CGAGATCAAC ACGTTGTTCC AGACGCTCAC CTCGATCGCC GAGAAGGTGG ATCCGGTCAA
GCTGAACCTG ACCCTGAGCG CGGCCGCGGA GGCGTTGACC GGGCTGGGCG ATAAGTTCGG
CGAGTCGATC GTCAACGCCA ACACCGTTCT GGATGACCTC AATTCGCGGA TGCCGCAGTC
GCGCCACGAC ATTCAGCAAT TGGCGGCTCT GGGCGACGTC TACGCCGACG CGGCGCCGGA
CCTGTTCGAC TTTCTCGACA GTTCGGTGAC CACCGCCCGC ACCATCAATG CCCAGCAAGC
GGAACTGGAT TCGGCGCTGT TGGCGGCGGC CGGGTTCGGC AACACCACAG CCGATGTCTT
CGACCGCGGC GGGCCGTATC TGCAGCGGGG GGTCGCCGAC CTGGTCCCCA CCGCCACCCT
GCTCGACACT TATAGCCCGG AACTGTTCTG CACGATCCGC AACTTCTACG ATGCCGATCC
GCTCGCTAAA GCGGGCGGCCG GTGGCGGGTAA CGGCTACTCG CTGAGGACGA ACTCAGAGAT
CCTATCCGGG ATAGGTATCT CCTTGTTGTC TCCCCTGGCG TTAGCCACCA ATGGGCGGC
AATCGGAATC GGACTGGTAG CCGGATTGAT AGCGTCGCCC CTCGCGGTGG CCGCAAATCT
```

FIG.4E

```
AGCGGGAGCC  CTACCCGGAA  TCGTTGGCGG  CGCGCCCAAT  CCCTATACCT  ATCCGGAGAA
TCTGCCGCGG  GTGAACGCTC  GCGGTGGCCC  GGGGGGCGCC  CCCGGTTGCT  GGCAGCCGAT
CACCCGGGAT  CTGTGGCCAG  CGCCGTATCT  CGCCGTATCT  ACCGGTGCCA  GCCTCGCCCC
GTACAACCAC  ATGGAGGTTG  GCTCGCCTTA  TGCAGTCGAG  TACGTCTGGG  GCCGTCAGT
AGGGGATAAC  ACGATCAACC  CA[TGA]AAATC  ACTGGAACCG  TCGTCAAACT  CGGCATCGTC  3383
TCGGTGGTGC  TGCTGTTCTT  CACGGTGATG  ATCATCGTGA  TTTTCGGTCA  GATGCGCTTC
GACCGGACTA  ATGGCTATAC  CGCGGAGTTC  AGCAATGTCA  GCGGGCTGCG  CCAAGGCCAG
TTTGTCCGTG  CTTCGGGGGT  AGAGATCGGC  AAGGTCAAAG  CACTACACCT  GGTCGACGGT
GGCCGTCGGG  TTCGGGTGGA  GTTCAATATC  GATCGTTCGG  GGTAACCGGT  TCAGTCCACG
ACCGCCCAGA  TCCGCTATTC  CGACCTGATC  TCTGCTGCCG  CCAGGTGGAC  CAAACGGGGT
GAGGGCAAGG  GGGCCAACGA  CGCGTTGATC  ACGTGGAGCT  TCATCCCATT  GTCCCGCACG
TCACCGGCCT  TGGATCTGGA  CGCGTTGATC  GGTGGTTTCA  AGCCGGTGTT  TCGGGCGTTG
GATCCCGCGA  AGGTGAACAA  CATCGCCAAC  GCGCTCATCA  CCGTCTTCCA  GGGCAAGGT
```

FIG.4F

```
GGCACCATAA  ACGACACCCT  CGACCAGACC  GCGCAACTGA  CCAGCCAGAT  CGCGGAGCGC
GATCAGGCGA  TCGGTGAGGT  TGTCAAGAAC  CTGAACATCG  TGCTGGACAC  CACGGTCAAG
CATCGAAAAG  AGTTCGACGA  GACGGTCAAT  AACTTGGAGA  ATCTGATCAC  TGGGCTGAGG
AACCACTCCG  ACCAGTTGGC  CGGCGGCCTC  GCGCACATCA  GCAACGGCGC  CGGCACGGTG
GCCGACCTGC  TTGCCGAGAA  TCGCACGTTG  GTGCCGCAAG  CCGTCAGCTA  CCTGGACGCT
ATTCAGCAAC  CGGTCATCGA  CCAGCGCGTC  GAGTTGGACG  ACCTGCTCCA  CAAGACGCCG
ACCGCGTGA   CGGGCGCTCGG ACGCGCCAAC  GGAACCTACG  GCGATTTCCA  GAACTTCTAC
CTCTGCGACC  TCCAGATCAA  GTGGAACGGA  TTCCAAGCCG  GAGGGCCGGT  CCGCACGGTG
AAGCTCTTTA  GCCAGCCGAC  GGGTAGGTGC  ACGCCGCAAT  GAGAACGCTG  GAACCACCCA
ACCGAATGCG  AATTGGGCTC  ATGGGCATCG  TCGTTGCGCT  GCTCGTTGTC  GCTGTGGGCC
AAAGCTTTAC  CAGTGTTCCC  ATGCTATTCG  CAAAGCCGAG  CTACTACGGC  CAGTTCACCG
ACTCCGGCGG  ACTGCACAAG  GGCGACAGGG  TACGCATCGC  CGGCTTGGGA  GTGGGCACCG
TGGAGGGGCT  CAAGATCGAC  GGCGACCACA  TCGTGGTCAA  GTTCTCCATC  GGCACCAACA
CCATCGGCAC  CGAGAGCCGC  CTAGCCATCC  GCACCGACAC  CATCCTGGGT  AGGAAAGTG
```

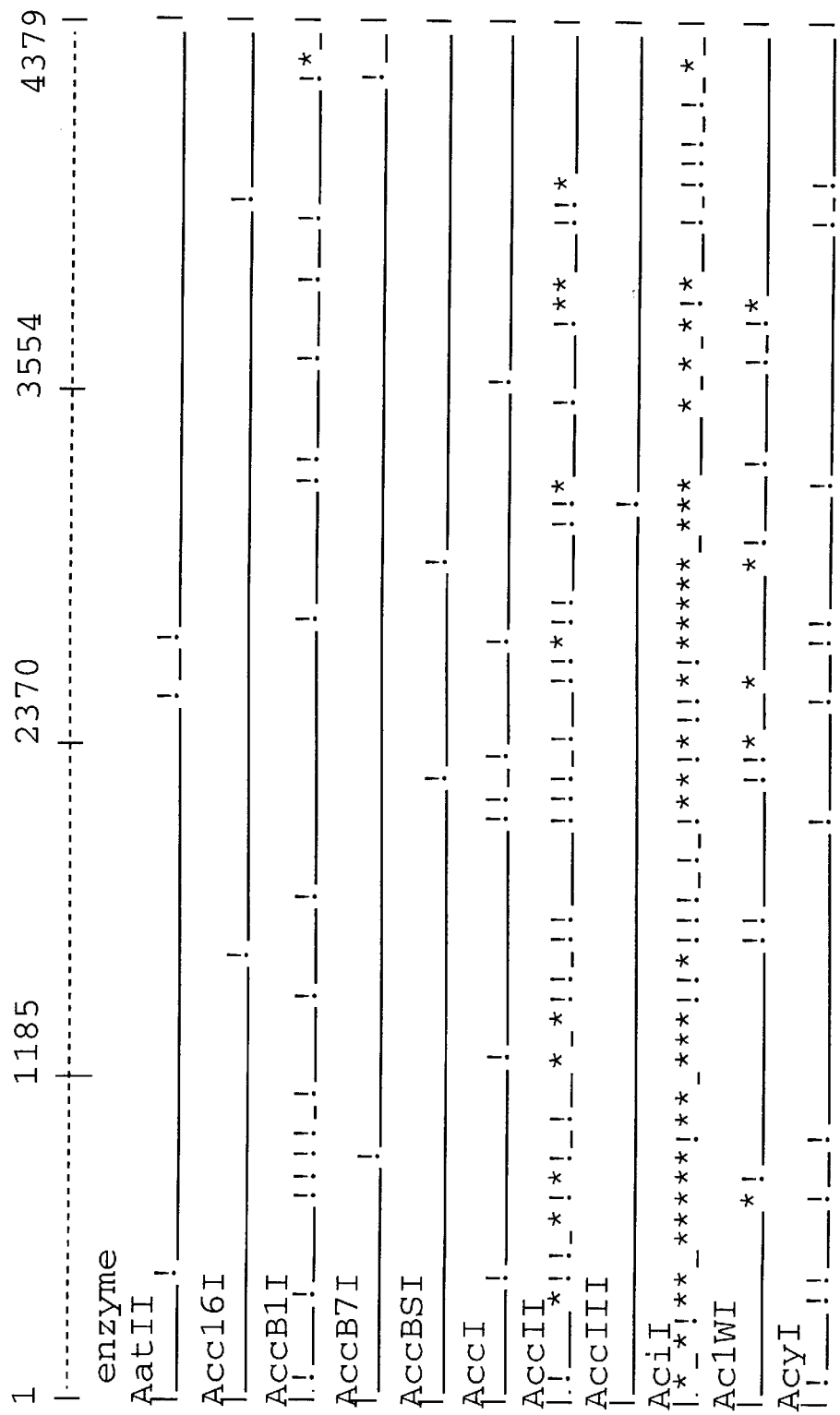
RESTRICTION MAP OF THE GENE ENCODING THE PROTIEN ASSOCIATED WITH CELL BONDING AND ENTRY
Area to print (<CR>=1 4739):
Chart of BCGINV-33 - Linear, Length 4739
1
1185
2370
3554
4379
enzyme
AatII
Acc16I
AccB1I
AccB7I
AccBSI
AccI
AccII
AccIII
AciI
Ac1WI
AcyI

CspI
CviJI
DdeI
DpnI
DraII
DraIII
DrdI
DsaI
EaeI
EagI
Eam1104I
Eam1105I
EarI

PmlI
PshAI
Psp124BI
Psp1406I
PspALI
PspEI
PspLI
PspN4I
PstI
PvuI
PvuII
RsaI
RsrII

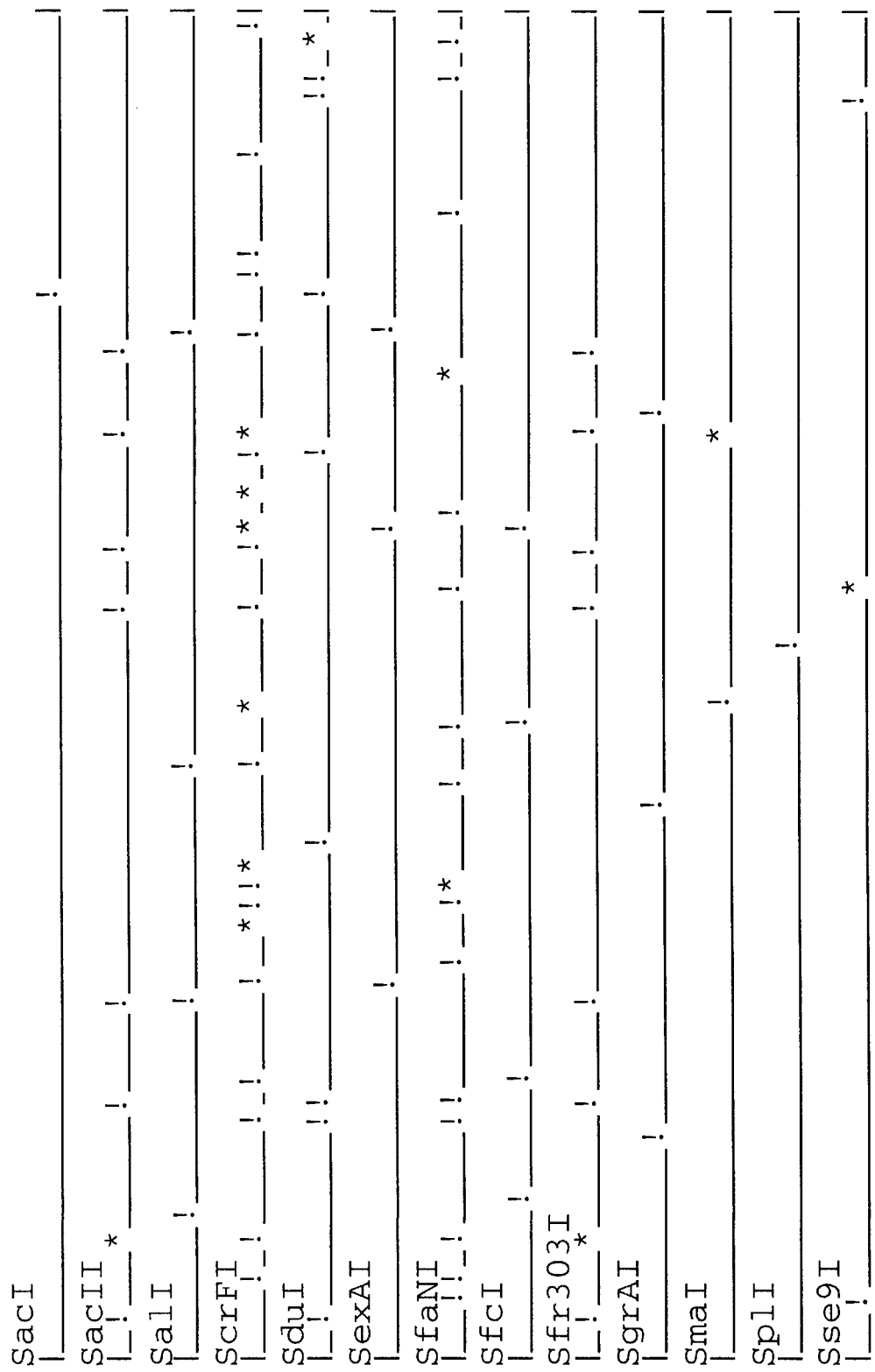

NUCLEIC ACID SEQUENCE OF THE DNA MOLECULES ENCODING THE MYCROBACTERIA PPROTEIN ASSOCIATED WITH CELL BINDING AND CELL ENTRY

```
        10         20         30         40         50         60         70
ATGTCTTTTG GTCCTTCTTG GAGGCCCTCA TCATCACTGC GATCGTCATG GTCAGCCACT GCTACTACGG 80         90        100        110        120        130        140
GTACGCCGCC GGTGGAGGCC CCGTCGGTGT CGGCGAGGCC GTCGGCCGAT CGATGCGTTT CTCGTTGGTC 150        160        170        180        190        200        210
TCGGTGCAGG TCGTTGTCCT GTTTGCAGCG TTGGCGCTCT ACGGTGTCGA CCCGAACTTC AATCTCACGG 220        230        240        2S0        260        270        280
TGTAGCCGCA TGACGACGCC GGGGAAGCTG AACAAGGCGC GAGTGCCGCC CTACAAGACG GCGGGTTTGG 290        300        310        320        330        340        350
GTCTAGTGCT GGTCTTCGCG CTCGTAGTTG CCTTGGTATA CCTGCAGTTT CGCGGGGAGT TCACGCCCAA 360        370        380        390        400        410        4Z0
GACGCAGTTG ACGATGCTGT CCGCTCGTGC GGGTTTGGTG ATGGATCCCG GGTCGAAGGT CACCTATAAC 430        440        450        460        470        480        490
GGGGTGGAGA TCGGGCGGGT AGACACCATC TCGGAGGTCA CACGTGACGG CGAGTCGGCG GCCAAGTTCA
```

FIG.6B

```
       500        510        520        530        540        550        560
TCTTGGATGT GGATCCGCGT TACATCCACC TGATTCCGGC AAATGTGAAC GCCGACATCA AGGCGACCAC 570        580        590        600        610        620        630
GGTGTTCGGC GGTAAGTATG TGTCGTTGAC CACGCCGAAA AACCCGCRLAA AGAGGCGGAT AACGCCAAAA 640        650        660        670        680        690        700
GACGTCATCG ACGTACGGTC GGTGACCACC GAGATCAACA CGTTGTTCCA GACGCTCACC TCGATCGCCG 710        720        730        740        750        760        770
AGAAGGTGGA TCCGGTCAAG CTGAACCTGA CCCTGAGCGC GGCCGCGGAG GCGTTGACCG GGCTGGGCGA 780        790        800        810        820        830        840
TAAGTTCGGC GAGTCGATCG SCAACGCCAA CACCGTTCTG GATGACCTCA ATTCGGCGGAT GCCGCAGTCG 850        860        870        880        890        900        910
CGCCACGACA TTCAGCAATT GGCGGGCTCTG GGCGACGTCT ACGCCGACGC GGCGCCCGGAC CTGTTCGACT 920        930        940        950        960        970        980
TTCGGGTGACC ACCGCCCGCA CCATCAATGC CCAGCAAGCG GAACTGGGATT CGGCGCTGTT 990       1000       1010       1020       1030       1040       1050
GGTTCGGCA ACADCACAGC CGATGTCTTC GACCGCGGGCG GGCCGTATCT GCA~CGGGGG
```

FIG.6C

```
1060        1070        1080        1090        1100        1110        1120
GTCGCCGACC  TGGTCCCCAC  CGCCACCCTG  CTCGACACTT  ATAGCCCGGA  ACTGTTCTGC  ACGATCCGCA 1130        1140        1150        1160        1170        1180        1190
ACTTCTACGA  TGCCGATCCG  CTCGCTAAAG  CGGCGGCCGG  TGGCGGTAAC  GGCTACTCGC  TGAGGACGAA 1200        1210        1220        1230        1240        1250        1260
CTCAGAGATC  CTATCCGGGA  TAGGTATCTC  CTTGTTGTCT  CCCCTGGCGT  TAGCCACCAA  TGGGGCGGCA 1270        1280        1290        1300        1310        1320        1330
ATCGGAATCG  GACTGGTAGC  CGGATTGATA  GCGTCGCCCC  TCGCGGTGGC  CGCAAATCTA  GCGGGAGCCC 1340        1350        1360        1370        1380        1390        1400
TACCCGGAAT  CGTTGGCGGC  GCGCCCAATC  CCTATACCTA  TCCGGAGAAT  CTGCCCGGGG  TGAACGCTCG 1410        1420        1430        1440        1450        1460        1470
CGGTGGCCCG  GGGGGCGCCC  CCGGTTGCTG  GCAGCCGATC  ACCCGGGATC  TGTGGCCAGC  GCCGTATCTG 1480        1490        1500        1510        1520        1530        1540
GTGATGGACA  CCGGTGCCAG  CCTCGCCCCG  TACAACCACA  TGGAGGTTGG  CTCGCCTTAT  GCAGTCGAGT 1550        1560        1570        1580
ACGTCTGGGG  CCGTCAGGTA  GGGGATAACA  CGATCAACCC  ATGA
```

FIG.7A

AMIDO ACID SEQUENCE OF MYCROBACTERIAL PROTEIN ASSOCIATED WITH CELL BINDING AND CELL ENTRY

```
ATG TCT TTT GGT CCT TCT TGG AGG CCC SCA 7CA TCA CTG CGA TCG TCA TGG $CA
MET Ser Phe Gly Pro Ser Trp Arg Pro Ser Ser S.r Lou Arg Ser Sor Trp Ser
                              27                                    54

GCC ACT GCT ACT ACG GGT ACG CCG ACG GTG GAG GCC CCG TCG GTG TCG GCG AGG
Ala Thr Ala Thr Thr Gly Thr Pro Pro Val Glu Ala Pro Ser Yal Sor Ala Arg
                              81                                   108

CCG TCG GCC GAT CGA TGC GTT TCT CGT TGG TCT C W TGC AGG TCG TTG TCC TGT
Pro S<r Ala Aap Arg Cyj Val Sor Arg Trp Ser C W Cya Arg Sor Lou Ser Cya
                             135                                   162

TTG CAG CGT TGG CGC TCT ACG GTG TCG ACC CGA ACT TCA ATC TCA CGG TGT AGC
Leu Gln Arg Trp Arq Ser Thr Val Sor Thr Arg 7hr Sor Ilo Sor Arg Cya Ser
                             189                                   216

CGC ATG ACG ACG CCG GGG AAG CTG AAC AAG GCG CGA GTG CCG CCC TAC AAG ACG
Arg MET Thr Thr Pro Gly Lya Lou Aan Lya Ala Arg Val Pro Pro Tyr Lya Thr
                             243                                   270
```

FIG.7B

```
GCG GGT TTG GGT CTA GTG CTG GTC TTC GCG CTC GTA GTT GCC TTG GTA TAC CTG
Ala Gly Lou Gly Lou Val Leu Val Pho Ala Lou Yal Val Ala Leu Val Tyr Leu
                                297                                  324

CAG TTT CGC GGG GAG TTC ACG CCC AAG ACG CAG TTG ACG ATG CTG TCC GCT CGT
Gln Phe Arg Gly Glu Pho Thr Pro Lya Thr Gln Leu Thr MET Lou Ser Ala Arg
                                351                                  378

GCG GGT TTG GTG ATG GAT CCC GGG TCG AAG GTC ACC TAT AAC GGG GTG GAG ATC
Ala Gly Lou Val M6T Aap Pro Gly Sor Lya Val Thr Tyr Aan Gly Val Glu Ilo
                                405                                  432

GGG CGG GTA GAC ACC ATC TCG GAG GTC ACA CGT GAC GGC GAG TCG GCG GCC AAG
Gly Arg Val Aap Thr Ile Sor Glu Val Thr Arg Aap Gly Glu Sor Ala Ala Lya
                                459                                  486

TTC ATC TTG GAT GTG GAT CCG CGT TAC ATC CAC CTG ATT CCG GCA AAT GTG AAC
Phe Ilo Lou Aap Val Aap Pro Arg Tyr Ilo Hia Lou Ile Pro Ala Acn Val Acn
                                513                                  540

GCC GAC ATC AAG GCG ACC ACG GTG TTC GGC GGT AAG TAT GTG TCG TTG ACC ACG
Ala Aap Ile Lya Ala Thr Thr Val Phe Gly Gly Lya Tyr Val Ser Leu Thr Thr
                                567                                  594
```

FIG. 7C

```
CCG AAA AAC CCG ACA AAG AGG CGG CCA ATA ACG CCA AAA GAC GTC ATC GAC GTA
Pro Lys Asn Pro Thr Lys Arg Arg Pro Ile Thr Pro Lys Asp Val Ile Asp Val
                                    621                                648

CGG TCG GTG ACC ACC GAG ATC AAC ACG TTG TTC CAG ACG CTC ACC TCG ATC GCC
Arg Ser Val Thr Thr Glu Ile Asn Thr Leu Phe Gln Thr Leu Thr Ser Ile Ala
                                    675                                702

GAG AAG GTG GAT CCG GTC AAG CTG AAC CTG ACC AGC GCG GCC GAG GCG TTG
Glu Lys Val Asp Pro Val Lys Leu Asn Leu Thr Ser Ala Ala Glu Ala Leu
                                    729                                756

ACC GGG CTG GGC GAT AAG TTC GGC ATG TCG GAG TCG ATC AAC GCC AAC ACC GTT CTG
Thr Gly Leu Gly Asp Lys Phe Gly Met Ser Glu Ser Ile Asn Ala Asn Thr Val Leu
                                    783                                810

GAT GAC CTC AAT TCG CGG ATG CCG CAG TCG CGC CAC GAC ATT CAG CAA TTG GCG
Asp Asp Leu Asn Ser Arg Met Pro Gln Ser Arg His Asp Ile Gln Gln Leu Ala
                                    837                                864

GCT CTG GGC GAC GTC TAC GCC GAC GCG GCG CCG GAC CTG TTC GAC TTT CTC GAC
Ala Leu Gly Asp Val Tyr Ala Asp Ala Ala Pro Asp Leu Phe Asp Phe Leu Asp
                                    891                                918
```

FIG.7D

```
                                                                              972
AGT TCG GTG ACC ACC GCC CGC ACC ATC AAT GCC CAG CAA GCG GAA CTG GAT TCG
Ser Ser Val Thr Thr Ala Arg Thr Ilo Aan Ala Gln Gln Ala Glu Lou Aap Ser

1026
GCG CTG TTG GCG GCC GCC GGG TTC GGC AAC ACC ACA GCC GAT GTC TTC GAC CGC
Ala Leu Leu Ala Ala Ala Gly Phe Gly Asn Thr Thr Ala Asp Val Phe Aap Arg

1080
GGC GGG CCG TAT CTG CAG CGG GTC GCC GAC CTG GTC CCC ACC GCC ACC CTG
Gly Gly Pro Tyr Leu Gln Arq Val Ala Aap Leu Val Pro Thr Ala Thr Leu

1134
CTC GAC ACT TAT AGC CCG GAA CTG TTC TGC ACG ATC CGC AAC TTC TAC GAT GCC
Leu Asp Thr Tyr Ser Pro Glu Leu Phe Cya Thr Ilo Arg Aan Phe Tyr Aap Ala

1188
GAT CCG CTC GCT AAA GCG GCC GGT GGC GGS AAC WC TAC TCG CTG AGG ACG
Asp Pro Leu Ala Ly~ Ala Ala Gly Gly Gly Aan Gly Tyr Ser Leu Arg Thr

1242
AAC TCA GAG ATC CTA TCC GGG ATA GGT ATC TCC TTG TCT CCC CTG GCG TTA
Asn Ser Glu Ile Leu Ser Gly Ile Gly Ile Ser Leu Leu Sar Pro Leu Ala Leu

1296
GCC ACC AAT GGG GCG GCA ATC GGA CTG GTA GCC W A TTG ATA GCG TCG
Ala Thr Asn Gly Ala Ala Ilo Gly Leu Val Ala Gly Lou Ile Ala Ser
```

FIG.7E

```
                                                                          1350
CCC CTC GCG GTG GCC GCA AAT CTA CCC GGA GCC CTA CCC GGA ATC GTT W  C  GGC
Pro Leu Ala Val Ala Ala A~n Leu Pro Gly Ala Leu Pro Gly Ile Val Gly Gly
                                                                          1404
GCG CCC AAT CCC TAT ACC TAT CCG GAG AAT CTG CCG CW  GTG AAC GCT CGC GGT
Ala Pro Asn Pro Tyr Thr Tyr Pro Glu Aan Leu Pro Arg Val Aan Ala Arg Gly
                                                                          1458
GGC CCG GGG GGC GCC CCC GGT TGC TGG CAG CCG ATC ACC CGG GAT CTG TGG CCA
Gly Pro Gly Gly Ala Pro Gly Cya Trp Gln Pro Ile Thr Arg Aap Leu Trp Pro
                                                                          1512
GCG CCG TAT CTG GTG ATG GAC ACC GGT GCC AGC CTC GCC CCG TAC AAC CAC ATG
Ala Pro Tyr Leu Val MET Asp Thr Gly Ala Ser Leu Ala Pro Tyr Aarn Hla MET
                                                                          1566
GAG GTT GGC TCG CCT TAT GCA GTC GAG TAC GTC TGG GGC CGT CAG GTA G  W  GAT
Glu Val Gly Ser Pro Tyr Ala Val Glu Tyr Val Trp Gly Arg Gln Val Gly Aap AAC ACG ATC AAC CCA TGA .
Asn Thr Ilo Aan Pro
```

FIG. 8A

```
BCGINV-33    1   ATCGTGGACGCTCTGCCCCGCAACCCCGCGGGGAAGTGTGCTCAAGACTGAACTGCGATTGC

BCGINV-33   62   GCTACGGGCGCCTGTGTGAATGTGTTGAAAGACGTTCTGCATCAGCTGGTTTCACGGAGAGAAG

BCGINV-33  123   GGAAAATCGACAGAAATTGTAACGTTTGCCCGCTATTGACGAAGGTTAAATGTGCGGATG

BCGINV-33  184   CCTTACACTCCTGGCTGGCCATCGGGTAGATTCCTGTGGTCTCCCGTTACTCCCTGTGAGTA

BCGINV-33  245   ACGAGGTGGCGGTCACACACCAAGGGTCGGGGCAAGGAAGAAGCGTGCGACATGATGCGCC

BCGINV-33  306   GCGGGCGCCGCGATACCCAGTTCGGGCGGCTTGAGGGAGCCGCGGTGACGTCGACAACGC

BCGINV-33  367   TTGGCGGTTACGTCCGCGACCAACTGCAAACCCCGCTGACCCTCGTCGGTGGATTCTTTCG
```

FIG.8B

```
BCGINV-33   428   CATGTGTGTGCTGACTGGAAAGGCGCTGTGTTCGCTGGCCGTTCCAGTGGGCGCGAGTTCATT
BCGINV-33   489   CTGCAGTGCTGGTTCATCATGCGGGTCGGATTTTTACCGACGATCATGGTCTCGATACCGC
BCGINV-33   550   TGACGGTGCTGTTGATCTTCACGCTCAATATTCTGCTGGCCCAGTTCGGCGCGGCAGACAT
BCGINV-33   611   CTCCGGTTCCGGCGCGGATCGGCGCGGTCACCCAGCTTGGCCCGCTGACAACGGTGCTG
BCGINV-33   672   GTGGTCGCCGCCCGGGATCCACGGCCCATCTGCGCCGACCTGGGTGCCCCGACCATCCGCG
BCGINV-33   733   AGGAAATCGACGCGATGAGGTGCTGGGCATCGATCCCATCCACCGTCTGGTGGTGCCGCG
BCGINV-33   794   GGTGCTCGCCTCGATGCTGTCGCCACGCTGCTCAACGGCTTGGTGATCACCGTCGGCCTG
```

FIG. 8C

```
BCGINV-33   855   GTCGGTGGCTTTCTCTTCGGTGTCTATCTGCAGAACGTTTCGGGGCGCCTACCTTGCCA
BCGINV-33   916   CGCTGACCTTGATCACCGGCCTGCCCGAGGTGGTCATCGCAACCATCAAAGCCGCAACGTT
BCGINV-33   977   CGGCCCTGATCGCGGGGCCTTGTCGGCTGCTATCGGGGGCTGACCGTCCGTGGCGGTTCCAAG
BCGINV-33  1038   GGTCTTGGCACCGCCGTCAACGAGACCGTGGTTGCTGTGTGTGATTGCCCTGTTCGCCGTCA
BCGINV-33  1099   ACGTGATCTTGACGACCATCGGTGTGCGATTCGGGACGGGCGCTGACATGTCGACCGCTG
BCGINV-33  1160   CTGTGCTGCGCGCCCGCTTCCCGGGGTCGCCAACCTTCGTCAATATGGAGGTGCGGC
BCGINV-33  1221   GGCCCGTGGATTGGACGAGGCCGGCCAGCTCACCTGTTCGCTTTGACCAGCATCGGGCAG
```

FIG.8D

```
BCGINV-33  1282  ATCGCGCACGCGCTGCGCTGCGCTACTACCGCAAGGAGACGCTGCGGCTGATCGCCCAGATCGGCA
BCGINV-33  1343  TGGGTACCGGCGCGGATGGCCGTCGTCGGCGGCACGGTCGCCATCGTGTTGGCTTTGTCACGCT
BCGINV-33  1404  GTCCGGGCAGCTCGCTGGTCGCAATCCAGGGCTTCGCCTGGGCAACATCGGTGTCGAG
BCGINV-33  1465  GCGT

FIG. 8E

```
BCGINV-33  1709  CGTTCCTGTCCCCGCAGATCACCACCACGGTGCTCTACGGGCAGTCGAACGGCACCTACGA
BCGINV-33  1770  GCATTACTTTCAAACGTTCCTGCGTCCCGACGATGTCTTTTGGTCCTTCTTGGAGGCCCTC
BCGINV-33  1831  ATCATCACTGCGATCGTCATGGTCAGCCACTGCTACTACGGGTACGCCGCGGTGGAGGCC
BCGINV-33  1892  CCGTCGGTGTCGGCGAGGCCGTCGGCCGATCGATGCGTTTCTCGTTGGTCTCGGTGCAGGT
BCGINV-33  1953  CGTTGTCCTGTTTGCAGCGTTGGGCGCTCTACGGTGTCGACCCGAACTTCAATCTCACGGTG
BCGINV-33  2014  TAGCCGCATGACGACGCCGGGGAAGCTGAACAAGGCCGAGTGCCGCCCTACAAGACGGCG
BCGINV-33  2075  GGTTTGGGTCTAGTGCTCTTCGCGCTCGTAGTTGCCTTGGTATACCTGCAGTTTCGCG
```

FIG.8F

BCGINV-33  2136  GGGAGTTCACGCCCAAGACGCAGTTGACGATGCTGTCCGCTCCGTGCCGGGTTTGGTGATGGA

BCGINV-33  2197  TCCCGGGTCGAAGGTCACCTATAAACGGGGGTGGAGATCGGGCGGGGTAGACACCATCTCGGAG
                 GGATCGAATTGCTGGCCCTTTGGCGGGGCGATTCGTGGAGATC

BCGINV-33        GCCCGTAGAAAGGTTCGCGGACGCGCCAAGGCCCGCGCAGACCGCCATAAACGTAGTTGACCA

BCGINV-33        GTCACACGTGACGGGCCGAGTCGGCGCGGCCAAGTTCATCTTGGATGTGGATCCGCGTTACATCC
                                                                   |||||||||||||||
                 GGTGGGTCTTTGACTGGGGCCCGGACACCGAACGAGGCGACCCGCGTTACATCC

BCGINV-33  2319  ACCTGATTCCGGCAAAATGTGAACGCCGACATCAAGGCGACCGGTGTTCGGCGGTAAGTA
                 |||||||||||||||||||||||||||||||||||||||||||||||||||||||||||
MTMCE      164   ACCTGATTCCGGCAAAATGTGAACGCCGACATCAAGGCGACCGGTGTTCGGCGGTAAGTA

BCGINV-33  2380  TGTGTCGTTGACCACGCCGAAAAAACCCGAACAAAGAGGCGGATAACGCCAAAAGACGTCATC
                 |||||||||||||||||||||||||||||||||||||||||||||||||||||||||||||
MTMCE      225   TGTGTCGTTGACCACGCCGAAAAAACCCGAACAAAGAGGCGGATAACGCCAAAAGACGTCATC

BCGINV-33  2441  GACGTACGGTCGGTGACCACCGAGATCAACACGTTGTTCCAGACGCTCACCTCGATCGCCG
                 ||||||||||||||||||||||||||||||||||||||||||||||||||||||||||||
MTMCE      286   GACGTACGGTCGGTGACCACCGAGATCAACACGTTGTTCCAGACGCTCACCTCGATCGCCG

FIG. 8G

```
BCGINV-33  2502  AGAAGGTGGATCCGGTCAAGCTGAACCTGACCCTGAGCGCGGCCGGAGGCGTTGACCGG
                 ||||||||||||||||||||||||||||||||||||||||||||||||||||||||||
MTMCE       347  AGAAGGTGGATCCGGTCAAGCTGAACCTGACCCTGAGCGCGGCCGGAGGCGTTGACCGG

BCGINV-33  2563  GCTGGGCGATAAGTTCGGCGAGTCGATCGTCAACGCCAACACCGTTCTGGATGACCTCAAT
                 ||||||||||||||||||||||||||||||||||||||||||||||||||||||||||||
MTMCE       408  GCTGGGCGATAAGTTCGGCGAGTCGATCGTCAACGCCAACACCGTTCTGGATGACCTCAAT

BCGINV-33  2624  TCGCGGATGCCGCAGTCGCGCCACGACATTCAGCAATTGGCGGCTCTGGGCGACGTCTACG
                 ||||||||||||||||||||||||||||||||||||||||||||||||||||||||||||
MTMCE       469  TCGCGGATGCCGCAGTCGCGCCACGACATTCAGCAATTGGCGGCTCTGGGCGACGTCTACG

BCGINV-33  2685  CCGACGCGCCGGCGCCGGACCTGTTCTCGACTTTCTCGACCAGTTCGGTGACCACCGCACCAT
                 ||||||||||||||||||||||||||||||||||||||||||||||||||||||||||
MTMCE       530  CCGACGCGCCGGCGCCGGACCTGTTCTCGACTTTCTCGACCAGTTCGGTGACCACCGCACCAT

BCGINV-33  2746  CAATGCCCAGCAAGCGGAACTGGATTCGGCGCGTGTTGGCGGGCCGGGTTCGGCCAACACC
                 ||||||||||||||||||||||||||||||||||||||||||||||||||||||||||||
MTMCE       591  CAATGCCCAGCAAGCGGAACTGGATTCGGCGCGTGTTGGCGGGCCGGGTTCGGCCAACACC

BCGINV-33  2807  ACAGCCGATGTCTTCGACCGGCGGGCCGCGTATCTGCAGCCGGGGGTCGCCCGACCTGGTCC
                 ||||||||||||||||||||||||||||||||||||||||||||||||||||||||||
MTMCE       652  ACAGCCGATGTCTTCGACCGGCGGGCCGCGTATCTGCAGCCGGGGGTCGCCCGACCTGGTCC
```

FIG.8H

```
BCGINV-33  2868  CCACCGCCACCCTGCTCGACACTTATAGCCCGGAACTGTTCTGCACGATCCCGCAACTTCTA
                 ||||||||||||||||||||||||||||||||||||||||||||||||||||||||||||||
    MTMCE   713  CCACCGCCACCCTGCTCGACACTTATAGCCCGGAACTGTTCTGCACGATCCCGCAACTTCTA

BCGINV-33  2929  CGATGCCGATCCGCTCGCTAAAGCGGGGCCGGTGGCCGGTAACGGCTACTCGCTGAGGACG
                 ||||||||||||||||||||
    MTMCE   774  CGATGCCGATCGACCTGACCCGCGCGGGCGCCGAGTGGTTCGCGGATCGGGCG

BCGINV-33  2990  AACTCAGAGATCC

FIG.8I

```
BCGINV-33  3234  AGCCGATCACCCGGGATCTGTGTGGCCAGCGCCGTATCTGGTGTGATGGACACCGGTGCCAGCCT

BCGINV-33  3295  GGCTAAGTGGCTACCTGACCCCCCAAGCGCCACCTTTGAAGCCGTGCTAGCCAAACT

BCGINV-33  3356  CGCCCCCGTACAACCACATGGAGGTTGGCTCGCCCTTATGCAGTCGACTACGTCTGGGCCGT

GGCCGCCCCGGCGCGACCAACCCCGACCACACCCGTCATCGACACCACCCCCGAT

BCGINV-33  3417  CAGGTAGGGATAACACGATCAACCCATGAAAATCACTGGAACCGTCGTCAAACTCGGCAT

GCGGGCCGCCATCGACCCGCGACACCCGCAGCCAAGCCCAACGCAACCACGGGCTGCTGG

BCGINV-33  3478  CGTCTCGGTGGTGCTGCTGTTCTTCACGGTGATGATCATCGTGATTTTCGGTCAGATGCGC

CCGGGCTGCGCGCGCTGATCCGTCATCCTGCCATCTCCGGCCCTCGGCCCAACTCCAG

BCGINV-33  3539  TTCGACCGGACTAATGGCTATACCGCGGAGTTCAGCAATGTCAGCGGGCTGCGCCAAGGCC

GTGCTGTGCGGTCCACGCCATGCCGAACGCGATCTCGAATTGGTTGGCACCGTATTCG

BCGINV-33  3539  AGTTTGTCCGTGCTTCGGGGTAGAGATCGGCAAAGCACTACACCTGGTCGACGG

GGATGGAACTGCTCGATAGCGATGCCTGCCGTTGCCGGCGTTGACATCGCGGACGA
```

FIG. 8J

```
BCGINV-33  3600  TGGCCGTCGGGTTCGGGGTGGAGTTCAATATCGATCGTTCGGTGCCGTTGTATCAGTCCACG
                 ACGCCTCGTGCTCGAGCACCCCGGCGACACCGTGCGCCACAGCGTCGAAGGCAGCCG
BCGINV-33  3661  ACCGCCCAGATCCGCTATTCCGACCTGATCGGTAACCGGTACGTGAGCTCAAACGGGGTG
                 CTGGCCGTCCGCGTCGACCAAGAGGAATTC
BCGINV-33  3722  AGGGCAAGGGGCCAACGATCTGCTGCCGCCAGGTGGACTCATCCCATTGTCCCGCACGTC
BCGINV-33  3783  ACCGGCCTTGGATCTGGACGCGTTGATCGGTGGTTTCAAGCCGGTGTTTCGGGCGTTGGAT
BCGINV-33  3844  CCCGCGAAGGTGAACAACATCGCCAACGCGCTCATCACCGTCTTCCAGGGGCAAGGTGGCA
BCGINV-33  3905  CCATAAACGACACCCTCGACCAGCCGCGCAACTGACCGGCAACCAGATCGCGGAGCGCGATCA
BCGINV-33  3966  GGCGATCGGTGAGGTTGTCAAGAACCTGAACATCGTGCTGGACACCACGGTCAAGCATCGA
```

FIG. 8K

```
BCGINV-33   4027  AAAGAGTTCGACGAGACGGTCAATAACTTGGAGAATCTGATCACTGGGCTGAGGAACCACT

BCGINV-33   4088  CCGACCAGTTGGCCGGCGGCCTCGCGCCACATCAGCAACGGCCCGGCACGGTGGCCGACCT

BCGINV-33   4149  GCTTGCCGAGAATCGCACGTTGGTGCGCAAGGCCGTCAGCTACCTGGACGCTATTCAGCAA

BCGINV-33   4210  CCGGTCATCGACCAGCGCGTCGAGTTGGACGACCTGCTCCACAAGAGCGCCGACCGCGTTGA

BCGINV-33   4271  CGGCGCTCGGACGCGCCAACGGAACCTACGGCGATTTCCAGAACTTCTACCTCTGCGACCT

BCGINV-33   4332  CCAGATCAAGTGGAACGGATTCCAAGCCGGAGGGCCGGTCCGCACGGTGAAGCTCTTTAGC

BCGINV-33   4393  CAGCCGACGGGTAGGTGCACGCCGCAATGAGAACGCTGGAACCACCCAACCGAATGCGAAT
```

FIG.8L

```
BCGINV-33  4454  TGGGCTCATGGGCATCGTCGTTGCGCTGCTCGTTGTGGGCCAAAGCTTTACCAGT

BCGINV-33  4515  GTTCCCATGCTATTCGCAAAGCCGAGCTACTACGGGCCAGTTCACCGACTCCGGGGACTGC

BCGINV-33  4576  ACAAGGGCGACAGGGTACGCCATCGCCCGGCTTGGGAGTGGGCACCGTGGAGGGGCTCAACAT

BCGINV-33  4637  CGACGGGCGACCACCATCGTGGTCAAGTTCTCCATCGGCACCAACACCATCGGCACCGAGAGC

BCGINV-33  4698  CGCCTAGCCATCCCGACCACCGACACCATCCTGGGTAGGAAAGTG
```

FIG. 11A  0.8% agarose gel
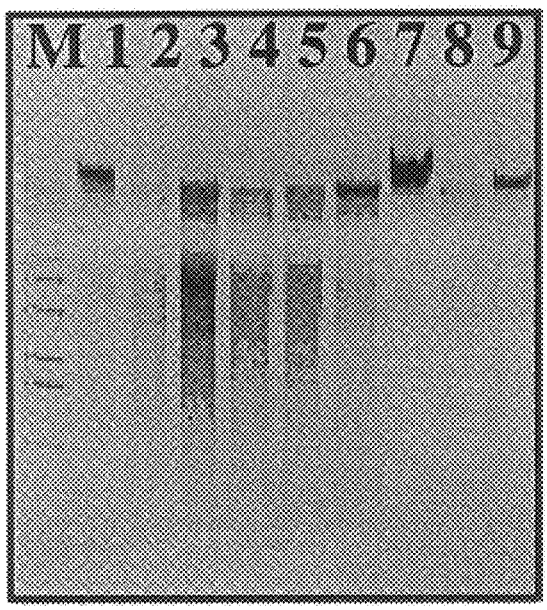
M: 1Kb marker
1. BCG uncut
2. BCG
3. TB188 (USA)
4. TB421 (Uganda)
5. TB458 (Brazil)
6. B. pertussis
7. B. catarrhalis
8. P. aeruginosa
9. H. influenzae
   (Eagan)
FIG. 11B  Southern blot
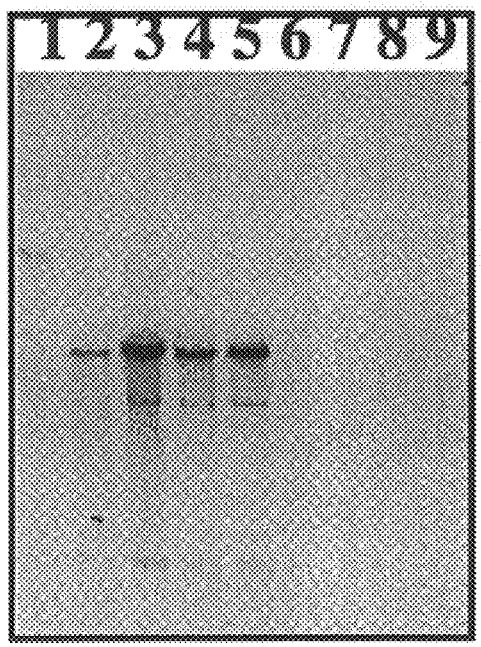
1. BCG uncut
2. BCG
3. TB188 (USA)
4. TB421 (Uganda)
5. TB458 (Brazil)
6. B. pertussis
7. B. catarrhalis
8. P. aeruginosa
9. H. influenzae
   (Eagan)

GENES ENCODING MYCOBACTERIAL PROTEINS ASSOCIATED WITH CELL BINDING AND CELL ENTRY AND USES THEREOF

FIELD OF INVENTION

The present invention relates to the field of molecular biology and is particularly concerned with genes encoding mycobacterial proteins associated with cell binding and cell entry and uses thereof.

BACKGROUND OF THE INVENTION

Tuberculosis (TB) is a major cause of mortality throughout the world, particularly in developing countries. There are about 8 to 9 million new cases of clinical disease reported every year and the number of deaths is estimated to be about 3 million. In the U.S. the trend of steady decline in TB has reversed and the problem is compounded by increasing numbers of drug-resistant strains. The tuberculosis complex is a group of four mycobacterial species that are genetically closely related. The three most important members are *Mycobacterium tuberculosis,* the major cause of human TB; *Mycobacterium africanum,* a major human pathogen in some populations; and *Mycobacterium bovis,* the cause of bovine TB. None of these mycobacteria is restricted in being pathogenic for a single host species.

In addition to being an important human disease, TB is also a major veterinary problem in many countries. Infection of cattle with *M. bovis* results in bovine TB and all animals showing any signs of infection are systematically slaughtered. The economic losses are thus extensive, and furthermore, cattle can serve as a reservoir for human disease.

In a majority of cases of infection, inhaled tubercle bacilli are ingested by phagocytic alveolar macrophages and are either killed or grow intracellularly to a limited extent in local lesions called tubercles. In this way the infection is limited and the primary sites of infection are walled off without any symptoms of disease being observed. Such individuals have a lifetime risk of about 10% for developing active disease. In a latter eventuality, bacilli spread from the site of infection in the lung, through the lung and via lymphatics or blood to other parts of the body producing characteristic solid caseous (cheese-like) necrosis in which bacilli survive. If the necrotic reaction expands breaking into a bronchus, or in the worst case, if the solid necrosis liquefy, a rapid proliferation of the bacilli occurs. The pathological and inflammatory processes set in motion then produce the characteristic weakness, fever, chest pain, cough and bloody sputum which are the hallmarks of active TB.

Effective treatment of TB with antibiotics exists. However, this is expensive and requires prolonged administration of a combination of drugs. There is a problem in compliance with the drug administration regime because of the extended time periods involved and this has contributed to the appearance of drug resistant strains. There is a recognized vaccine for TB which is an attenuated form of *M. bovis,* known as BCG (bacilla Calmette Guérin). This strain was developed in 1921 and the basis for its attenuation is still not known (ref. 1—throughout this application, various references are cited in parentheses to describe more fully the state of the art to which this invention pertains. Full bibliographic information for each citation is found at the end of the specification, immediately preceding the claims. The disclosure of these references are hereby incorporated by reference into the present disclosure). The efficacy of BCG as a TB vaccine is a subject of controversy and has been estimated in various trials to be anywhere between 0 and 70%.

The molecular basis for the virulence and pathogenesis of *M. tuberculosis* have not been extensively described. Some virulence factors, particularly those related to the sigma factors have been recently identified (ref. 2). *M. tuberculosis* can enter non-phagocytic cells in culture, such as HeLa cells (ref. 3) and once inside can multiply and survive. Recently, a DNA molecule (1535 bp long) from a strain of *M. tuberculosis* (H37Ra) was reported to mediate the entry of the bacterium and its survival in mammalian cells (ref. 4). This DNA fragment when introduced into a non-pathogenic strain of *E. coli* is able to confer invasiveness to the bacterium, and survival for up to 24 hours in human macrophages. The mce gene (mycobacterial cell entry) gene was mapped to an Open Reading Frame (ORF) extending from position 182 to 810 on the 1535 bp DNA fragment mentioned above and encodes a protein of molecular weight between 22 and 27 kDa.

Mycobacterial infection may lead to serious disease. It would be advantageous to provide genes encoding proteins of mycobacteria associated with cell binding and cell entry for the provision of these proteins as antigens in immunogenic preparations including vaccines, carriers for other materials including antigens and the generation of diagnostic reagents. The genes encoding mycobacterial proteins associated with cell binding and cell entry are particularly desirable and useful in the specific identification and diagnosis of mycobacteria and for immunization against disease caused by mycobacterial infection.

SUMMARY OF INVENTION

In the present invention, the gene of *Mycobacterium bovis* encoding the protein associated with cell binding and cell entry has been isolated and cloned and found to encode a protein of molecular weight about 45 to about 60 kDa. Corresponding genes have been detected in other members of the tuberculosis complex, including *Mycobacterium tuberculosis.*

Accordingly, in one aspect of the invention, there is provided an isolated nucleic acid molecule encoding a Mycobacterium protein having a molecular weight of about 45 to about 60 kDa associated with cell binding and cell entry of a Mycobacterium strain.

The Mycobacterium strain is a strain of the tuberculosis complex, which includes a strain of *M. tuberculosis* and *M. bovis* as well as the other members of the complex, including *M. africanum.*

The protein associated with cell binding and cell entry encoded by the nucleic acid molecule may have an amino acid composition as shown in Table 2.

The nucleic acid molecule of the invention may have a restriction map as shown in FIG. 5. This restriction map is for the gene from the *M. bovis* strain BCG. The nucleic acid molecule also may have the restriction map of the corresponding genes in other mycobacteria from the tuberculosis complex.

The nucleic acid molecule may have a DNA sequence as shown in FIG. 6 (SEQ ID No: 2) for *M. bovis* strain BCG or the sequence of the corresponding gene in other mycobacteria from the tuberculosis complex.

The nucleic acid molecule also may encode an amino acid sequence as shown in FIG. 7 (SEQ ID No: 3) for *M. bovis* strain BCG or the sequence encoding the corresponding protein in other mycobacteria from the tuberculosis complex.

In another aspect of the invention, there is provided an isolated DNA molecule amplifiable by polymerase chain reaction (PCR) by a pair of primers having the sequence of primers 4879 (SEQ ID No: 12) and 4882 (SEQ ID No: 15); or 4879 (SEQ ID No: 12) and 4865 (SEQ ID No: 11); or 4879 (SEQ ID No: 12) and 4812 (SEQ ID No: 10). The DNA molecule may be from a member of the tuberculosis complex, particularly *M. tuberculosis* and *M. bovis.*

In an additional aspect, the present invention includes a vector adapted for transformation of a host, comprising a nucleic acid molecule or DNA molecule provided herein. The invention further includes a plasmid containing the gene of a strain of Mycobacterium encoding the protein associated with cell binding and cell entry having the identifying characteristics of plasmid pBCGcepX having ATCC Deposit No. 97511.

The vector may be adapted for expression of the encoded protein in a heterologous or homologous host, in either a lipidated or non-lipidated form. Accordingly, a further aspect of the present invention provides an expression vector adapted for transformation of a host comprising a nucleic acid molecule or DNA molecule as provided herein and expression sequences operatively coupled to the nucleic acid molecule or DNA molecule for expression by the host of the protein associated with cell binding and cell entry. The expression sequences may include a promoter and a nucleic acid portion encoding a leader sequence for secretion from the host of the protein. The expression sequences may also include a nucleic acid portion encoding a lipidation signal for expression from the host of a lipidated form of the protein. The host may be selected from, for example, *Escherichia coli,* Bordetella, Bacillus, Haemophilus, Moraxella, fungi, yeast or baculovirus and Semliki Forest virus expression systems may be used.

In an additional aspect of the invention, there is provided a transformed host containing an expression vector as provided herein. The invention further includes a recombinant mycobacterial protein associated with cell binding and cell entry producible by the transformed host as provided herein.

In accordance with another aspect of the invention, an immunogenic composition is provided which comprises at least one active component which is a nucleic acid molecule, DNA molecule or protein as provided herein and a pharmaceutically acceptable carrier therefor or vector therefor. The at least one active component produces an immune response when administered to a host.

The immunogenic compositions provided herein may be formulated as vaccines for in vivo administration to a host. For such purpose, the compositions may be formulated as a microparticle, capsule, ISCOM or liposome preparation. The immunogenic composition may be provided in combination with a targeting molecule for delivery to specific cells of the immune system or to mucosal surfaces. The immunogenic compositions of the invention (including vaccines) may further comprise at least one other immunogenic or immunostimulating material and the immunostimulating material may be at least one adjuvant or at least one cytokine.

In accordance with another aspect of the invention, there is provided a method for generating an immune response in a host, comprising the step of administering to a susceptible host, such as a primate including a human, an effective amount of the immunogenic composition as recited above. The immune response may be a humoral or a cell-mediated immune response and may provide protection against disease caused by mycobacteria.

In a further aspect, there is provided a live vector for delivery of the mycobacterial protein associated with cell binding and cell entry to a host, comprising a vector containing the nucleic acid molecule or DNA molecule as described above. The vector may be selected from Salmonella, adenovirus, poxvirus, vaccinia and poliovirus.

The nucleic acid and DNA molecules provided herein are useful in diagnostic applications. Accordingly, in a further aspect of the invention, there is provided a method of determining the presence, in a sample, of nucleic acid encoding a mycobacterial protein associated with cell binding and cell entry, comprising the steps of:

(a) contacting the sample with a nucleic acid or DNA molecule as provided herein to produce duplexes comprising the nucleic acid or DNA molecule and any nucleic acid molecule encoding the protein present in the sample and specifically hybridizable therewith; and (b) determining the production of the duplexes.

In addition, the present invention provides a diagnostic kit for determining the presence, in a sample, of nucleic acid encoding protein of a strain of Mycobacterium associated with cell binding and cell entry, comprising:

(a) a nucleic acid or DNA molecule as provided herein;

(b) means for contacting the nucleic acid or DNA molecule with the sample to produce duplexes comprising the nucleic acid or DNA molecule and any nucleic acid encoding the protein present in the sample and hybridizable with the nucleic acid or DNA molecule; and (c) means for determining production of the duplexes.

The present invention additionally includes the use of a gene amplification detection assay for the detection of mycobacteria. Accordingly, in this aspect of the invention, there is provided a method for the detection of a species of mycobacteria in a sample such as tissue or body fluids, which comprises:

providing a pair of primers which are primers 4879 (SEQ ID No: 12) and 4882 (SEQ ID No: 15); or 4879 (SEQ ID No. 12) and 4865 (SEQ ID No: 11); or 4879 (SEQ ID No: 12) and 4812 (SEQ ID No: 10);

contacting the sample with the primers;

performing a polymerase chain reaction to amplify an amplifiable DNA sequence encoding a mycobacterial protein associated with cell binding or cell entry, and detecting the amplified DNA sequence which indicates the presence of a species of Mycobacterium in the sample.

The present invention further includes, in a further aspect, an oligonucleotide primer selected from the group consisting of primers 4879 (SEQ ID No: 12), 4882 (SEQ ID No: 15), 4865 (SEQ ID No: 11) and 4812 (SEQ ID No: 10).

In addition, the present invention includes, in a further aspect, a method of forming a substantially pure recombinant mycobacterial protein associated with cell binding and cell entry which comprises transforming a host with a vector as described above, growing the transformed host to express the protein and isolating and purifying the protein free from other proteinaceous and cellular material.

In a further aspect of the invention, there is provided an isolated and purified mycobacterial protein of a Mycobacterium species associated with cell binding and cell entry having a molecular weight of about 45 to about 60 kDa. Such protein may be derived from the Mycobacterium, or by recombinant means as described above.

The proteinaceous material provided herein also may be included in the immunogenic composition as the active component thereof.

The invention further includes the use of the nucleic acid molecules, DNA molecules and proteins provided herein as medicines. The invention additionally includes the use of the nucleic acid molecules, DNA molecules and proteins provided herein as an active pharmaceutical substance and in the preparation of medicaments for protection against disease caused by infection by Mycobacterium.

Advantages of the present invention include:
an isolated and purified nucleic acid molecule encoding a mycobacterial protein of a strain of Mycobacterium associated with cell binding and cell entry;
Mycobacterial proteins associated with cell binding and cell entry; and
diagnostic kits and immunological reagents for specific identification of mycobacteria.

BRIEF DESCRIPTION OF DRAWINGS

The present invention will be further understood from the following General Description and specific Examples with reference to the drawings, in which:

FIG. 4 shows the nucleotide sequence (SEQ ID No: 1) of a DNA molecule containing the gene encoding the mycobacterial protein associated with cell binding and cell entry;

FIG. 6 shows the coding sequence (SEQ ID No: 2) of the gene encoding the mycobacterial protein associated with cell binding and cell entry;

FIG. 7 shows the nucleotide sequence (SEQ ID No: 2) and the deduced amino acid sequence (SEQ ID No: 3) of the mycobacterial protein associated with cell binding and cell entry;

FIG. 8 shows a comparison of the DNA sequences of the *M. bovis* gene encoding a mycobacterial protein associated with cell binding and cell entry (BCGINV-33) (SEQ ID No: 2) and a DNA fragment of *M. tuberculosis* described in the art (MTMCE) (SEQ ID No: 17);

* and FIG. 11, containing panels A and B, shows the specific identification of mycobacteria from other bacteria.

GENERAL DESCRIPTION OF THE INVENTION

Figure 1:
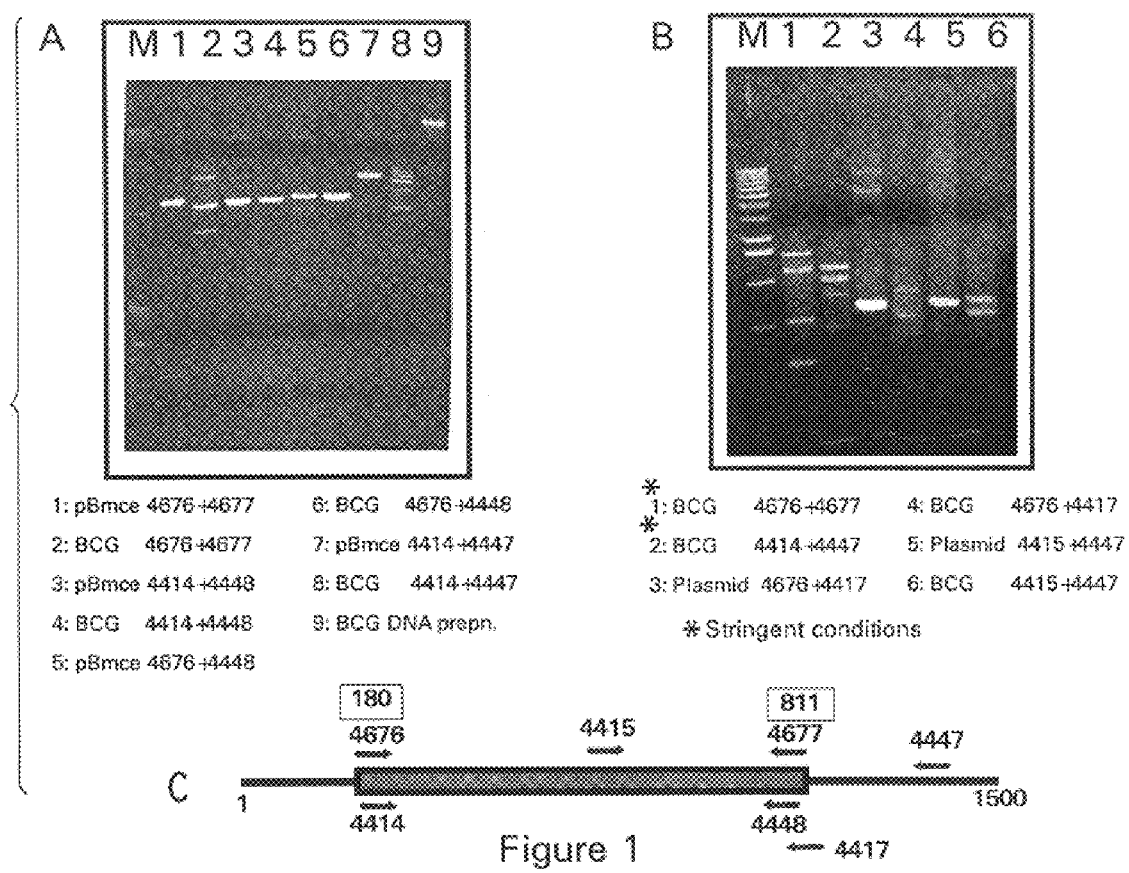
FIG. 1, containing panels A, B and C shows the amplification of genes encoding mycobacterial proteins associated with cell binding and cell entry by the polymerase chain reaction procedure.

Referring to FIG. 1, there is illustrated the PCR amplification of the gene encoding the mycobacterial protein associated with cell binding and cell entry from *M. bovis* BCG. The gene is sometimes referred to herein as the mce gene. The sequence of the various primers shown in FIG. 1 are listed in Table 1 below.

Two primers, 4676 (SEQ ID No: 4) and 4677 (SEQ ID No: 5) corresponding to the 5' and 3' ends of the ORF1 sequence (181 bp to 810 bp) encoding the mce of *Mycobacterium tuberculosis*, which is part of the 1535 bp insert, were designed according to the sequence published by Arruda et al (ref. 4) to amplify the corresponding mce gene from BCG. PCR experiments with BCG DNA and subsequent electrophoresis did not yield the expected DNA band (panel A, Lane 2; panel B, Lane 2; FIG. 1), whereas the control plasmid pZX7, (labelled as pBmce Lane 1, panel A, FIG. 1) gave the expected amplification product. Another pair of oligomers, 4414 (SEQ ID No: 6) and 4448 (SEQ ID No: 9), which prime in the ORF at sequences a few bases removed from the ends (approximately 20), do give the expected product of the correct size for both BCG and the control plasmid. Other amplifications were carried out using primer pairs 4676 (SEQ ID No: 4)/4448 (SEQ ID No: 9), 4414 (SEQ ID No: 6)/4447 (SEQ ID No: 8) and 4415 (SEQ ID No: 16)/4447 (SEQ ID No: 8), the products were analyzed by gel electrophoresis and the results shown in FIG. 1. Only primer pairs 4676/4448 and 4414/4448 yield expected amplification products from PCR reactions on BCG DNA, based on the published *Mycobacterium tuberculosis* mce gene sequence. The control experiments using plasmid pZX7 (labelled as pBmce or "plasmid" in FIG. 1) all gave the expected sized amplified fragment.

To clone the corresponding gene from *M. bovis* BCG, the gene was identified on particular fragments of the *M. bovis* genome by Southern blot hybridization using an mce gene-specific probe.

Figure 2A:
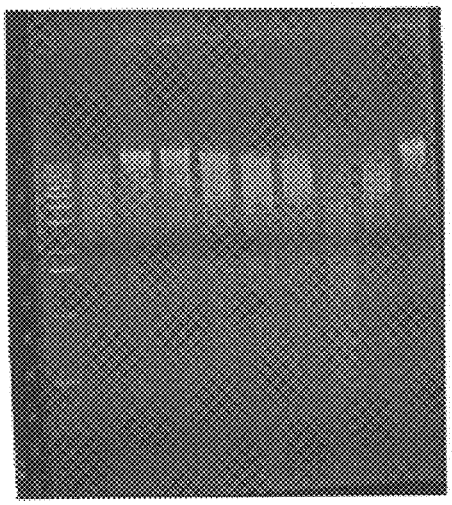
FIG. 2, containing panels (A) and (B), shows a Southern blot analysis of the genes encoding mycobacterial proteins associated with cell binding and cell entry.
Figure 2B:
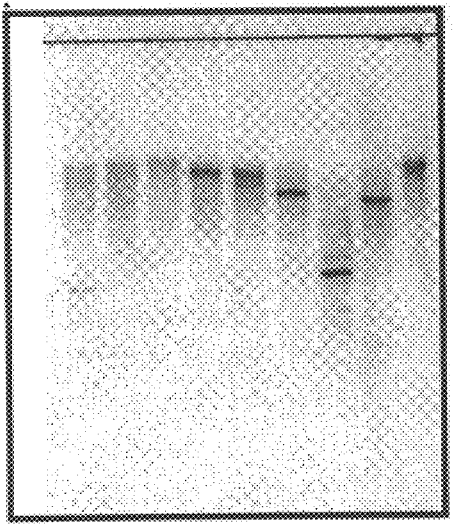
Figure 3:
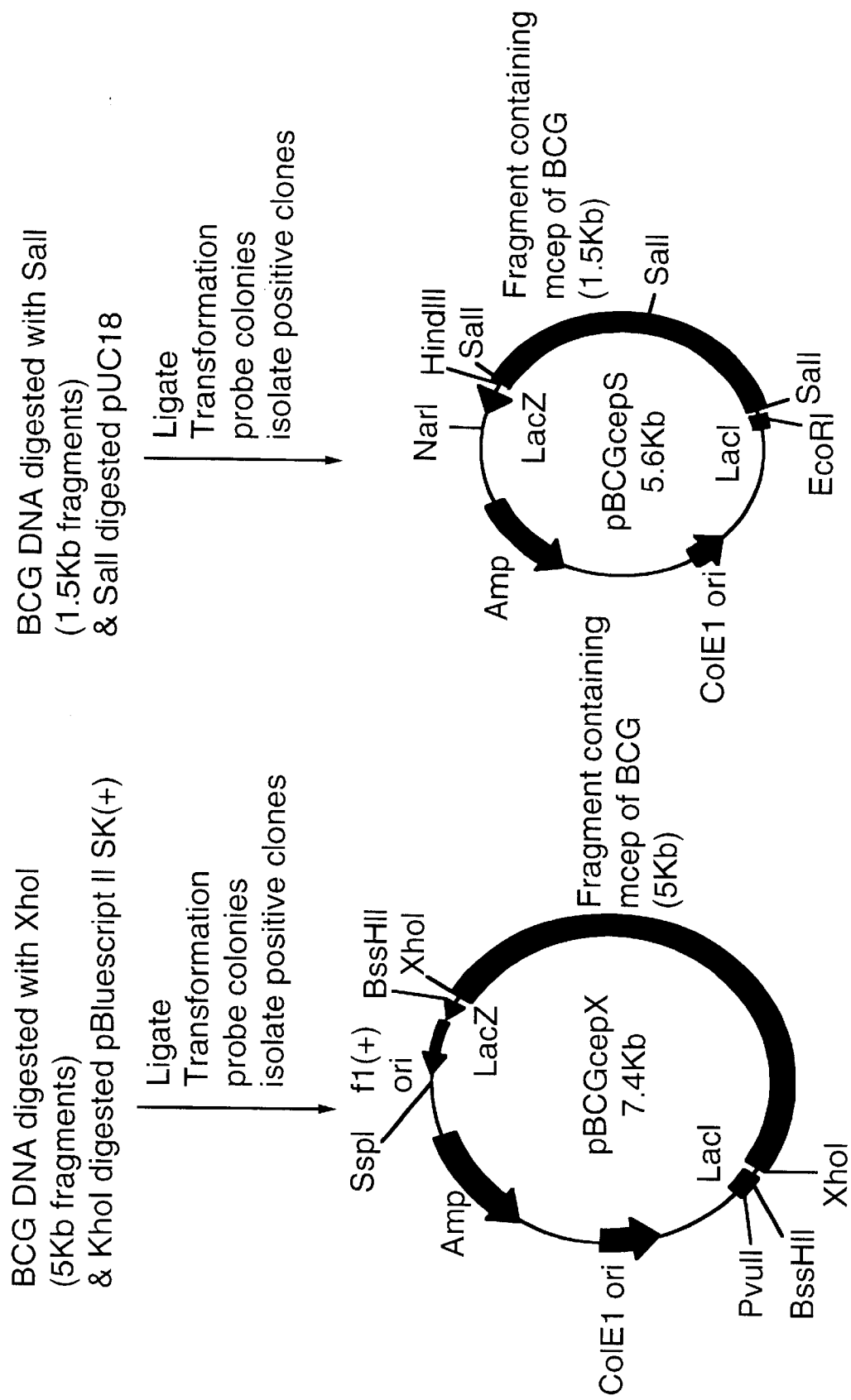
FIG. 3 illustrates plasmids containing genes encoding mycobacterial proteins associated with cell binding and cell entry.
Figure 5D:
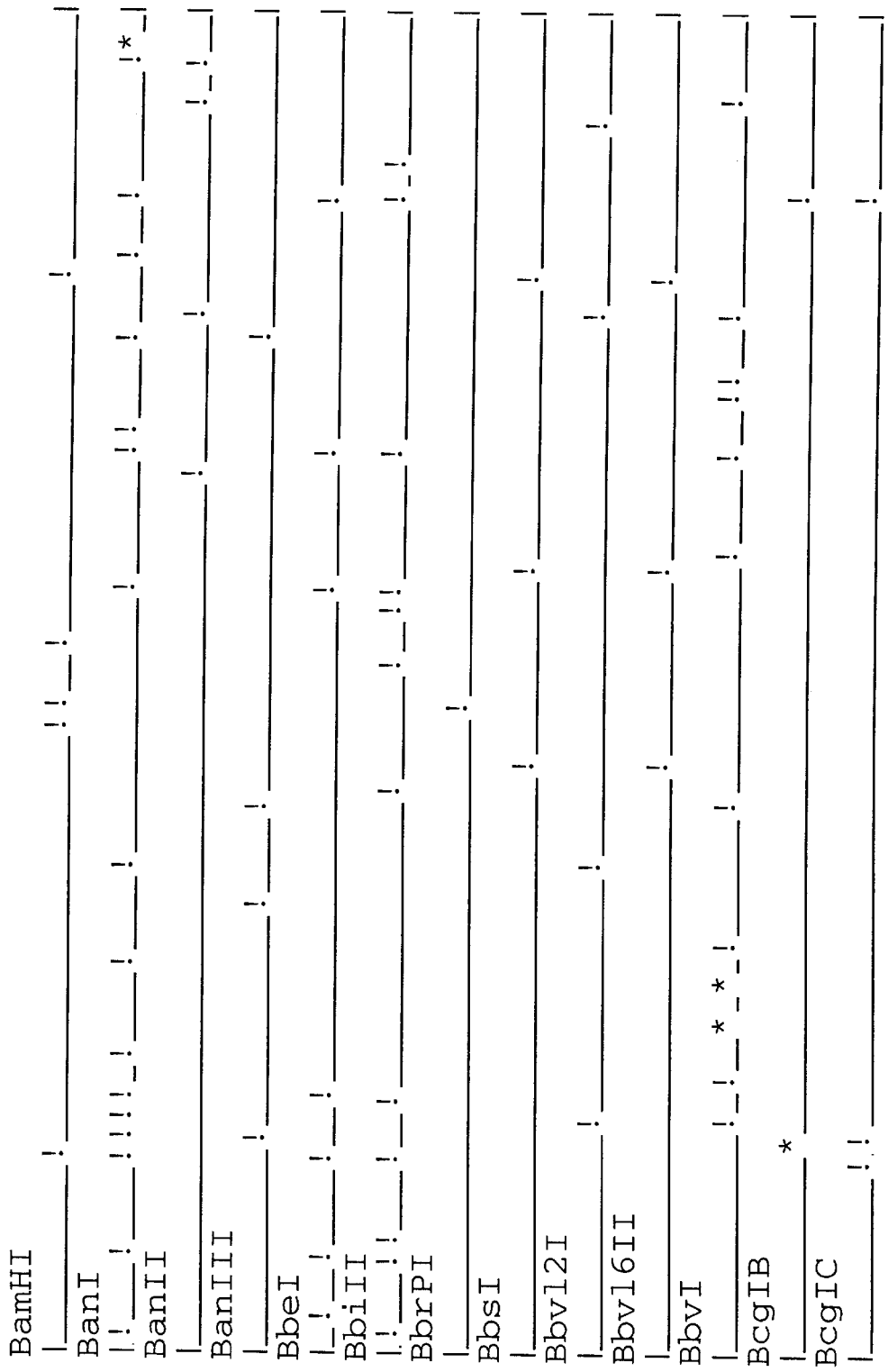
FIG. 5 shows a restriction enzyme analysis of the gene encoding the mycobacterial protein associated with cell binding and cell entry.
Figure 5E:
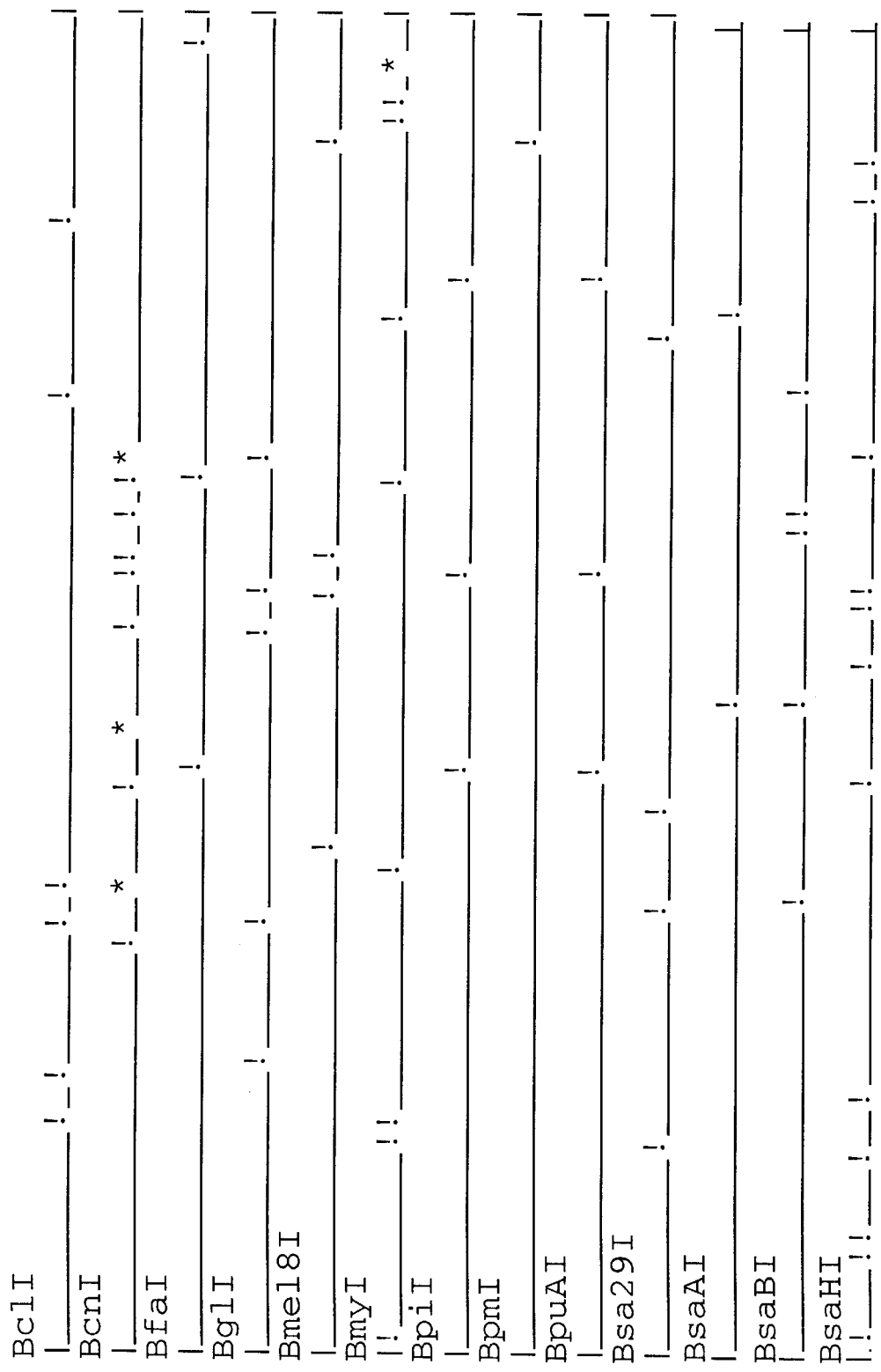
Figure 5G:
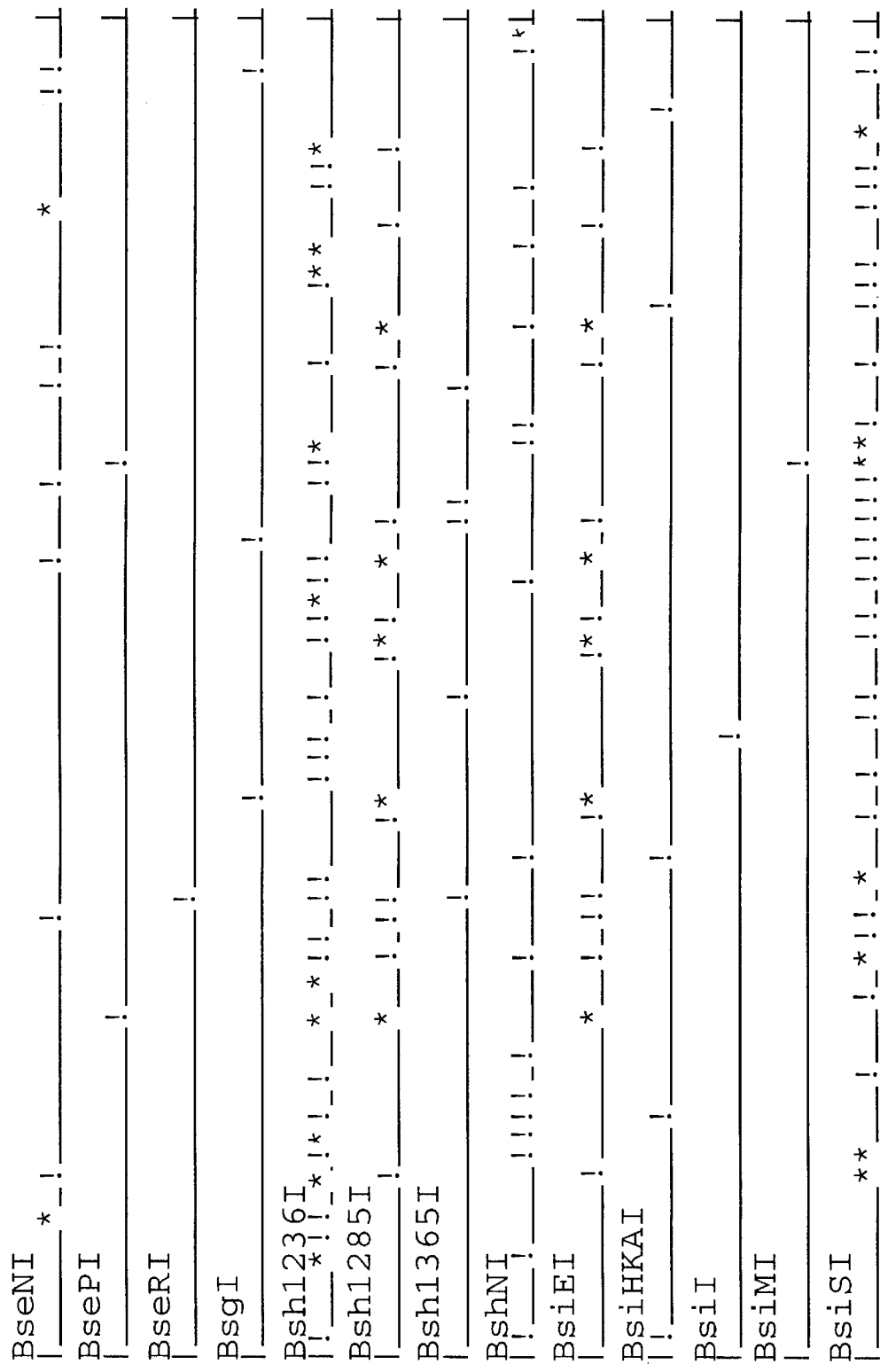
Figure 5I:
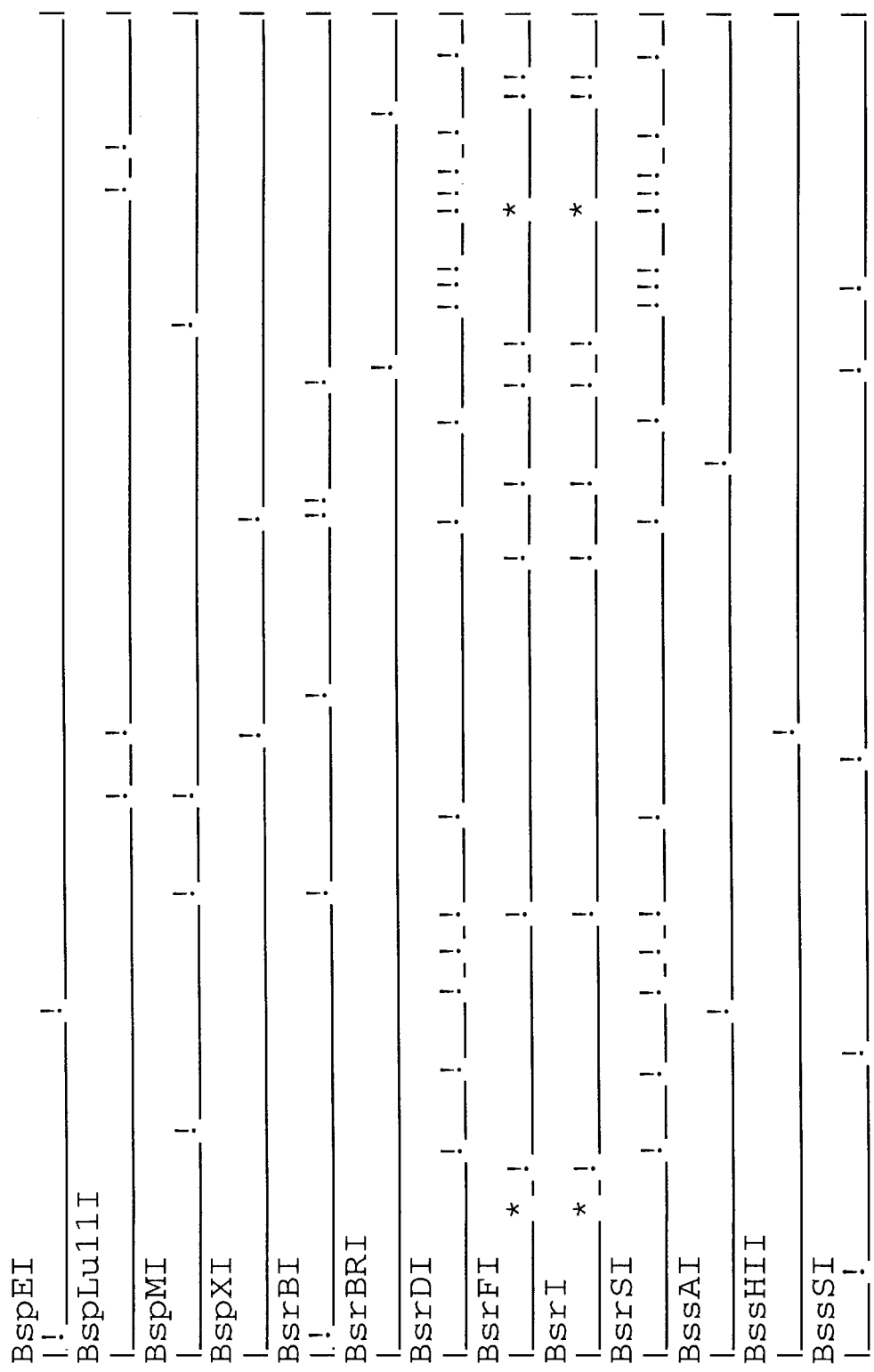
Figure 5J:
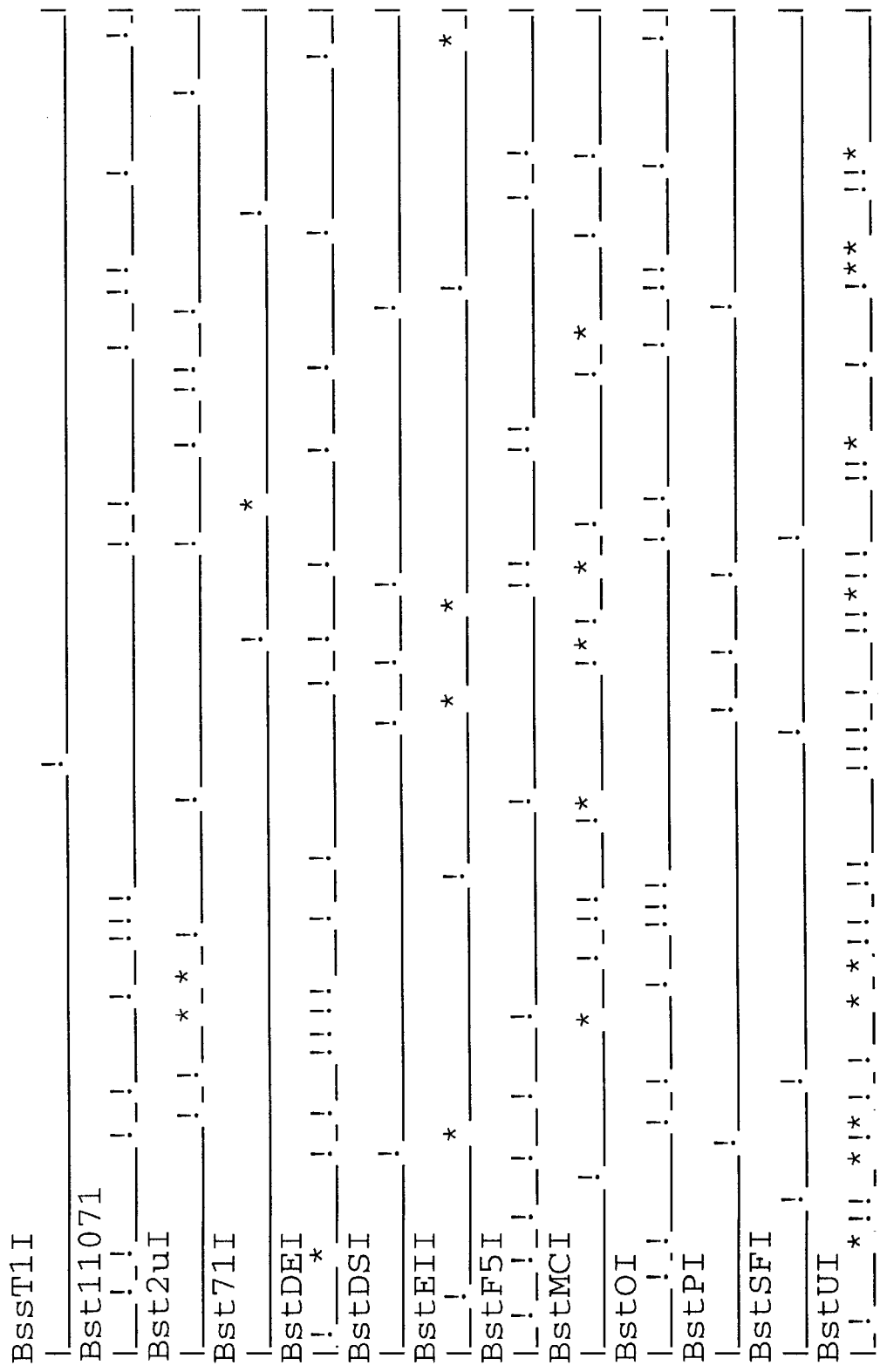
Figure 5M:
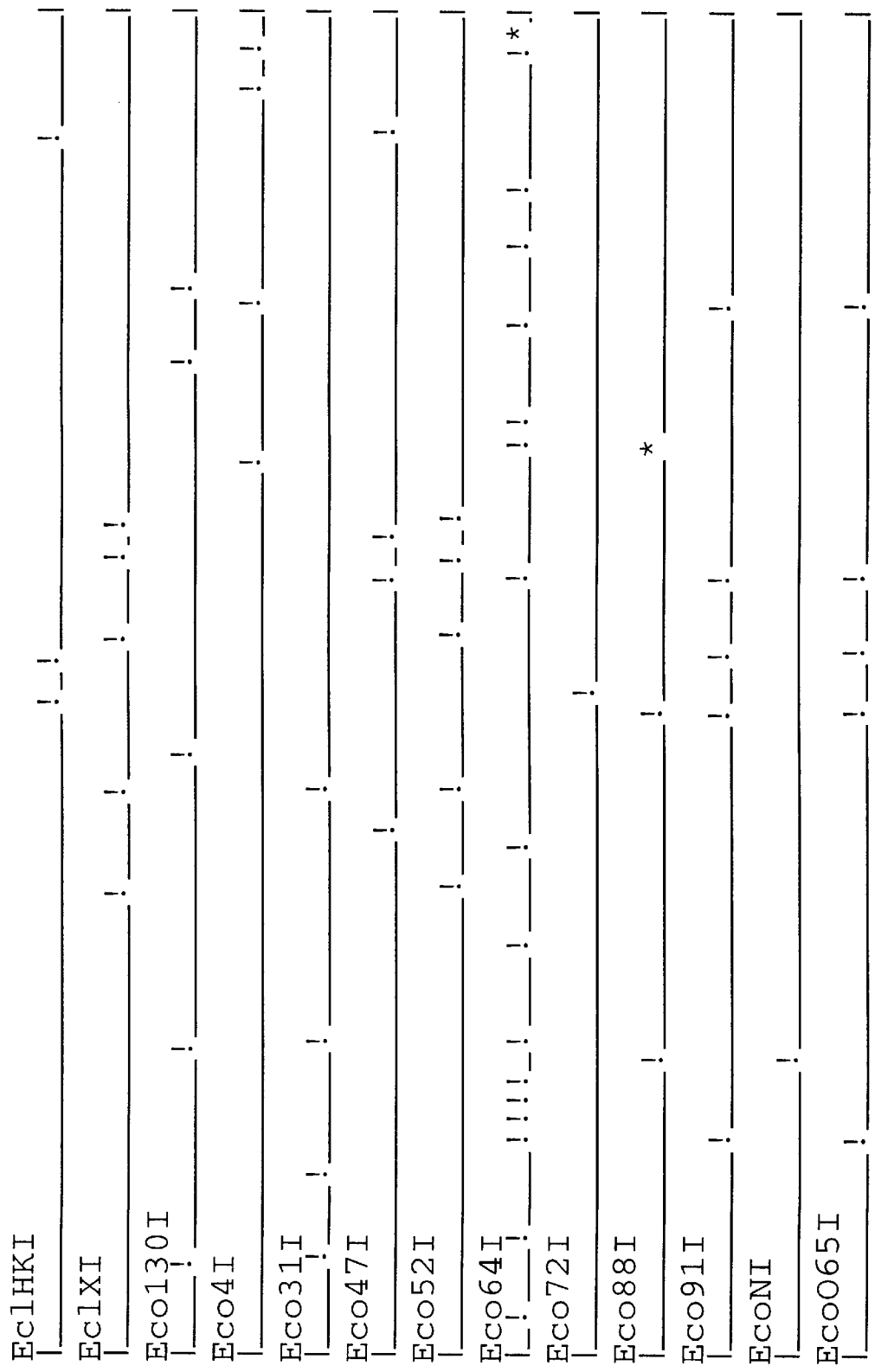
Figure 5Q:
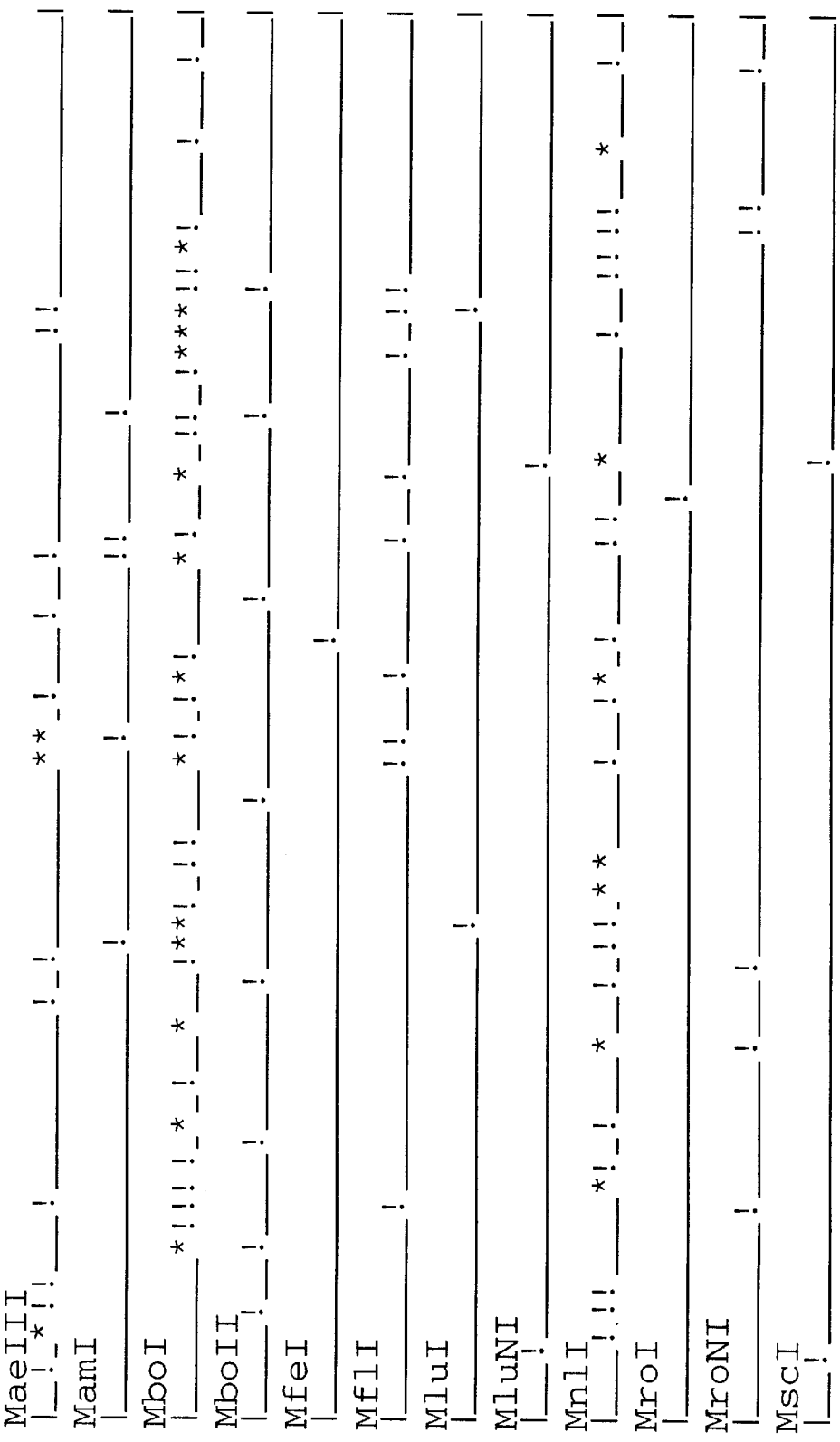
Figure 5W:
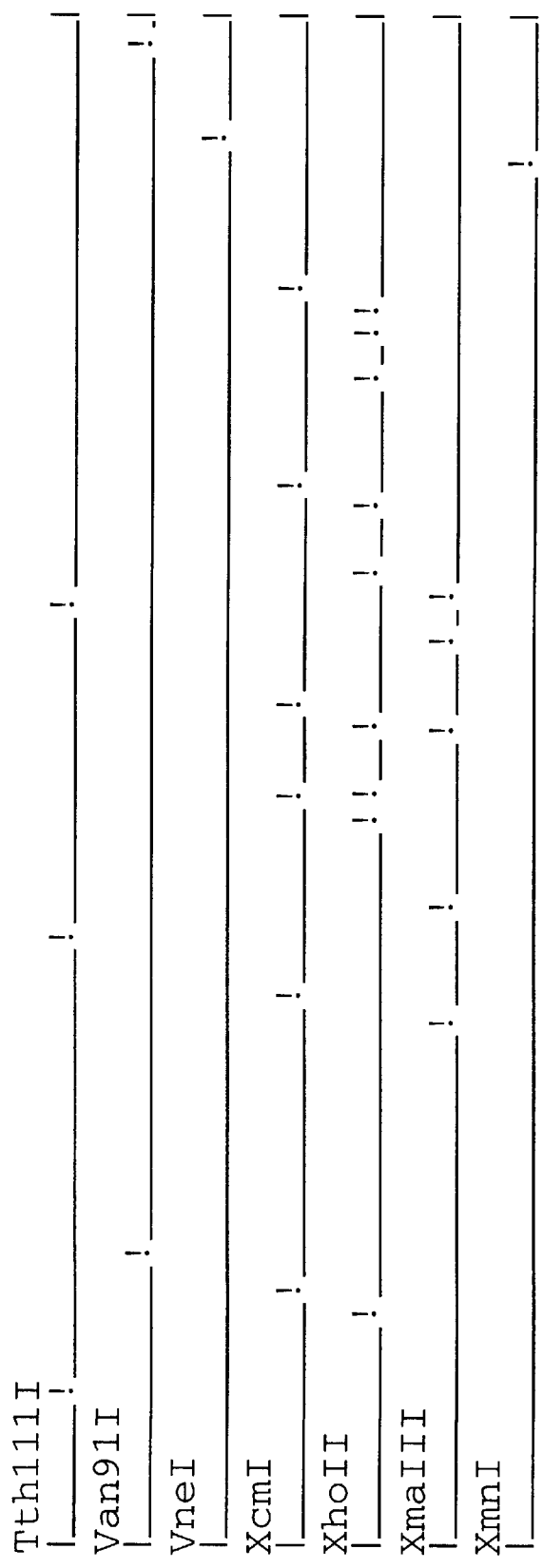

Restriction enzyme digestion of *M. bovis* BCG DNA and subsequent Southern blot analysis using a PCR amplified product (primer pairs 4414/4448; Lane 2; panel A, FIG. 1) as a probe, indicated the presence of the mce gene on 1.5 kb and 5 kb fragment of Sal I and Xho I digests (FIG. 2). The corresponding bands were cut out and ligated into suitably digested pUC18 and pBluescript II sk(+) plasmids respectively. The libraries obtained after transformation of competent *E. coli* cells were probed for the mce gene by hybridization and two positive clones were identified. These clones were grown, plasmid isolated and analyzed to yield two plasmids: plasmid pBCGcepX contained an approximately 5 kb DNA insert hybridizing to mce gene-specific probe and another plasmid pBCGcepS containing a 1.5 kb Sal I insert also hybridizing to the mce gene-specific probe (FIG. 3).

The inserts of plasmids pBCGcepS and pBCGcepX were sequenced by the primer walking technique. Plasmid pBCGcepS contained a 1.5 kb insert (shown in dark box, FIG. 3) containing the *M. bovis* BCG gene and also an irrelevant tandem 1.5 kb Sal I insert (shown in grey box, FIG. 3). The sequence data from the inserts were aligned using a sequence assembly program from Intelligenetics. It was found that the 1.5 kb SalI insert of pBCGcepS was an internal fragment of the larger pBCGcepX clone. The complete sequence of the 4740 bp DNA fragment cloned into plasmid pBCGcepX (SEQ ID No: 1) is illustrated in FIG. 4.

The ORF of the mce gene of *Mycobacterium tuberculosis* previously described (ref. 4) is an internal sequence of the BCG gene provided herein. The corresponding *Mycobacterium tuberculosis* ORF starts at position 2336 and is identical to the *M. bovis* BCG sequence for the next 602 bp. The two sequences then diverge and the *Mycobacterium tuberculosis* sequence ends in a stop codon 21 bp along, whereas, the BCG ORF continues for another 423 bp. The putative start of the *M. bovis* BCG gene is also 505 bp upstream of the GTG start sequence of the *Mycobacterium tuberculosis* mce gene. The sequences are, therefore, quite different. The alignment of nucleic acid sequences illustrating the coding sequence identity and the differences in 5' and 3' sequences between the inserts of plasmid pZX7 (ref. 4) and pBCGcepX are shown in FIG. 8.

A chart listing endonuclease digestion sites for the 4.7 kb insert in pBCGcepX is shown in FIG. 5.

The 4740 bp DNA sequence was searched for possible open reading frames (ORFs). An ORF was found between positions 1802 and 3383 of the sequence (FIG. 4). The DNA sequence of this open reading frame (SEQ ID No: 2) is shown in FIG. 6. The ORF starts at ATG and there is a stop codon at TGA. The open reading frame is 1581 nucleotides long. Other putative ATG and GTG start codons in the DNA sequence encoding the mycobacterial protein of *M. bovis* BCG associated with cell binding and cell entry are shown boxed in FIG. 4. The start codon of the MceP protein proposed by Arruda et al., (ref. 4) is shown in FIG. 4 at nucleotide position 2336. The open reading frame (SEQ ID No: 2) encodes a protein of 527 amino acids and a molecular weight of about 55 kDa. This may be a precursor protein with a signal sequence at the N-terminus which may be removed during post-translational processing. The sequence of the protein of *M. bovis* BCG associated with cell binding and cell entry is shown in FIG. 7 (SEQ ID No: 3). The translation frames for the ORFI of *Mycobacterium tuberculosis* mce gene (ref. 4) and the *M. bovis* BCG gene described herein are the same. Therefore, the MceP protein of *Mycobacterium tuberculosis* is also an internal polypeptide of the protein from *M. bovis* BCG provided herein.

As explained above, a prior art gene involved in mediating cell entry of *M. tuberculosis* H37Ra (and described in reference 4) is quite different than that provided herein isolated for the first time from *M. bovis* BCG.

Figure 9:
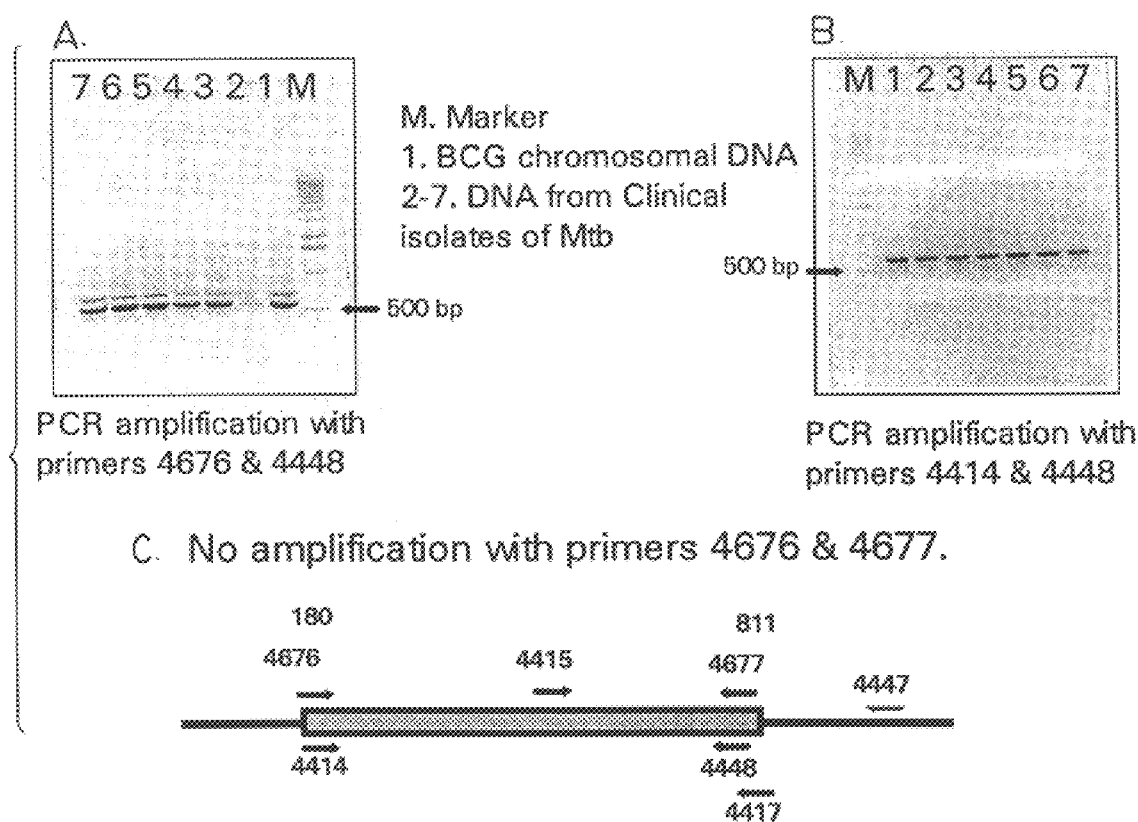
FIG. 9 shows the identification of genes encoding the mycobacterial protein associated with cell binding and cell entry in clinical isolates of *M. tuberculosis;*
Figure 10:
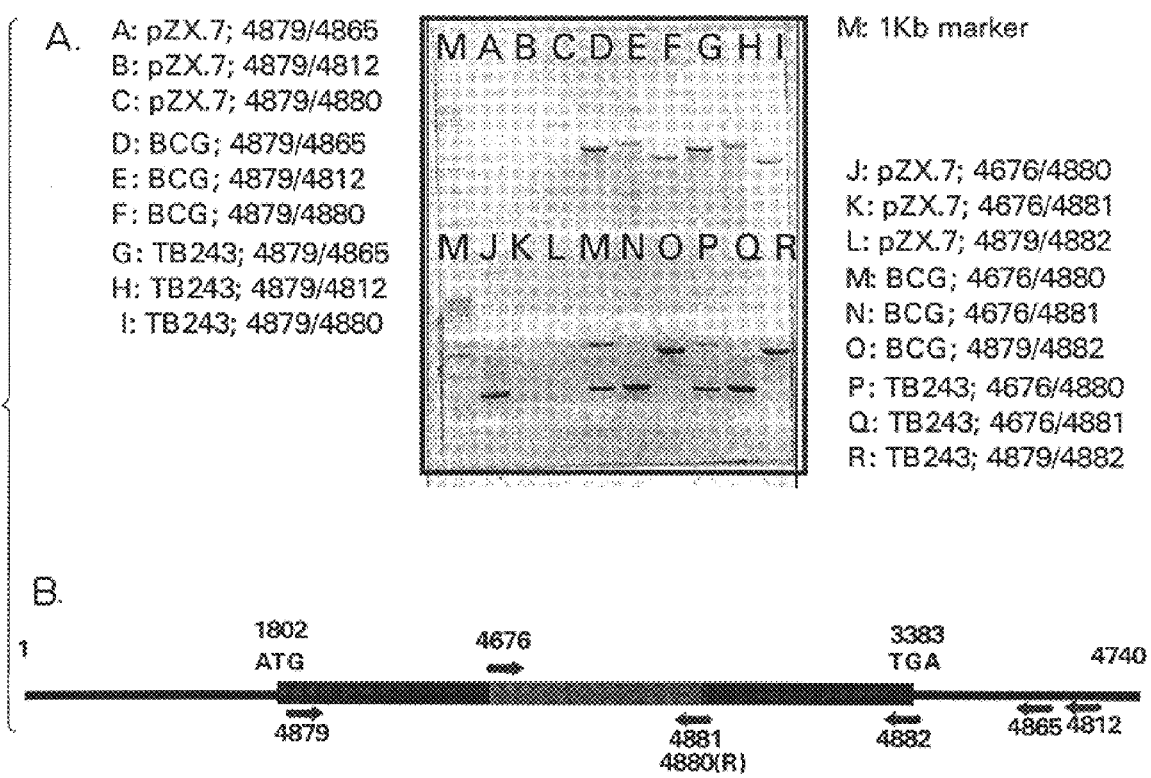
FIG. 10 shows the further characterization of genes encoding the mycobacterial protein associated with cell binding and cell entry in other strains of *Mycobacterium tuberculosis.

Referring to FIG. 9, there is illustrated the identification of a gene corresponding to the gene of *M. bovis* BCG as provided herein from clinical isolates of *M. tuberculosis*. The DNA from twelve different clinical isolates of *M. tuberculosis* was subjected to PCR using primer combination 4676/4677 (the positions relative to the published mce gene of *M. tuberculosis* is shown at the bottom of FIG. 9) and no amplification of a discrete product of the expected size was observed. In contrast, however, primer combinations 4676/4448 and 4414/4448 did yield fragments of about 600 bp (FIG. 9), which is the correct size as predicted from the sequence of the gene encoding the protein associated with cell binding and cell entry as provided herein of *M. bovis* BCG. Further PCR reactions using DNA from a *M. tuberculosis* clinical isolate TB243 (from the USA) were performed using primer combinations based upon the sequence of the inserted fragment in pBCGcepX derived from *M. bovis* BCG. Primer 4879 is designed based upon a sequence 3' to the putative stop codon at position 3383 (bottom of FIG. 10). PCR amplification using primer pair 4879/4865 in reactions with BCG and *M. tuberculosis* (TB243) DNA give a single amplified product of the expected size (approximately 2.6 kb). PCR amplification using primer pair 4879/4812 also produced a band of the correct size but mispriming also produced other smaller products. Primer 4880 is designed to span the stop codon sequence in ORF1 described for the *M. tuberculosis* H37Ra mce gene (ref. 4). Therefore, primer pair 4879/4880 should not yield an approximately 1.1 kb amplified product. Although misprimed products were observed, no 1.1 kb product was obtained in PCR reactions containing *M. bovis* BCG or *M. tuberculosis* clinical isolate DNA (Lanes F and I, FIG. 10). None of these primer combinations produced any PCR products using plasmid pZX7 as the template (ref. 4). This is expected since the insert in this plasmid is devoid of the 5' sequences observed for the *M. bovis* BCG gene encoding the mycobacterial protein associated with cell entry and cell binding, as provided herein. PCR reactions with other primer combinations such as 4676/4880, 4676/4881 and 4879/4882 were performed with plasmid pZX7 as well as with *M. bovis* BCG and *M. tuberculosis* (TB243) DNA. Amplification of pZX7 with oligomer pair 4676/4880 (primer 4880 spans a sequence flanking the stop codon of the published *M. tuberculosis* mce ORF) yielded the expected sized DNA fragment. PCR amplification with the same primer pair leads to several amplification products from the BCG and *M. tuberculosis* clinical isolate DNA and was most likely due to non-specific priming. PCR using primers 4676/4881 (the latter spanning the sequence corresponding to 4880, in *M. bovis* BCG) yielded the correct sized band in *M. bovis* BCG, and *M. tuberculosis*, while no product was obtained for plasmid pZX7 (lanes N, Q and K, FIG. 10). Again, the products expected based on the BCG sequence were observed on PCR amplification using primers 4879 and 4882 (the latter constituting a sequence spanning the stop codon of the *M. bovis* BCG sequence).

It was clear from the PCR amplification experiments on *M. bovis* BCG DNA, using primers designed from the sequence of *M. tuberculosis* H37Ra (ref. 4), that the *M. bovis* BCG gene was different. The gene encoding a mycobacterial protein associated with cell binding and cell entry as provided herein is present in a number of clinical isolates from *M. tuberculosis* and encodes a protein of molecular weight of about 55,000. Thus, a prior art gene encoding a protein involved in mediating cell entry of *M. tuberculosis* H37Ra (ref. 4) may be a naturally occurring truncated variant of the more frequently encountered gene encoding a mycobacterial protein associated with cell binding and cell entry having a molecular weight of about 45,000 to about 60,000 and may reflect the different source of the prior art gene and the gene provided herein and may be due to cloning artifacts of the prior art work.

In a diagnostic embodiment, the gene of the present invention is useful for specifically distinguishing mycobacteria from other pathogens. The use of the 4.7 kb insert of pBCGcepX as a probe in Southern blots of Xho I restriction enzyme digests of DNA from a number of *M. tuberculosis* clinical isolates and other pathogens, such as *B. pertussis, M. catarrhalis, Pseudomonas aeruginosa* and *H. influenzae* demonstrate the absence of homologous sequences in non-mycobacterial organisms. In contrast, all of the *M. tuberculosis* isolates tested have the specific 5 kb fragment described above and this distinguishes them from such other pathogenic organisms, (FIG. 11).

It is clearly apparent to one skilled in the art, that the various embodiments of the present invention have many applications in the fields of vaccination, diagnosis, treatment of, for example, mycobacterial infections and the generation of immunological and other diagnostic reagents. A further non-limiting discussion of such uses is further presented below.

1. Vaccine Preparation and Use

Immunogenic compositions, suitable to be used as vaccines, may be prepared from immunogenic mycobacterial protein associated with cell binding and cell entry encoded by the nucleic acid molecules as well as the nucleic acid molecules disclosed herein. The vaccine elicits an immune response which produces antibodies, including anti-cell binding and cell entry protein antibodies and cell-mediated immune responses.

Immunogenic compositions including vaccines may be prepared as injectables, as liquid solutions or emulsions. The protein and nucleic acid molecules may be mixed with pharmaceutically acceptable excipients which are compatible therewith. Such excipients may include, water, saline, dextrose, glycerol, ethanol, and combinations thereof. The immunogenic compositions and vaccines may further contain auxiliary substances such as wetting or emulsifying agents, pH buffering agents, or adjuvants to enhance the effectiveness of the vaccines. Immunogenic compositions and vaccines may be administered parenterally, by injection subcutaneously, intradermally or intramuscularly. Alternatively, the immunogenic compositions formed according to the present invention, may be formulated and delivered in a manner to evoke an immune response at mucosal surfaces. Thus, the immunogenic composition may be administered to mucosal surfaces by, for example, the nasal or oral (intragastric) routes. Alternatively, other modes of administration including suppositories and oral formulations may be desirable. For suppositories, binders and carriers may include, for example, polyalkylene glycols or triglycerides. Oral formulations may include normally employed incipients such as, for example, pharmaceutical grades of saccharine, cellulose and magnesium carbonate. These compositions may take the form of solutions, suspensions, tablets, pills, capsules, sustained release formulations or powders and contain 1 to 95% of the protein and/or nucleic acid molecules.

The vaccines are administered in a manner compatible with the dosage formulation, and in such amount as will be therapeutically effective, protective and immunogenic. The quantity to be administered depends on the subject to be treated, including, for example, the capacity of the individual's immune system to synthesize antibodies, and if needed, to produce a cell-mediated immune response. Precise amounts of active ingredient required to be administered depend on the judgment of the practitioner. However, suitable dosage ranges are readily determinable by one skilled in the art and may be of the order of micrograms of the protein and/or nucleic acid molecules. Suitable regimes for initial administration and booster doses are also variable, but may include an initial administration followed by subsequent administrations. The dosage of the vaccine may also depend on the route of administration and will vary according to the size of the host.

The nucleic acid molecules encoding the mycobacterial protein associated with cell binding and cell entry may be used directly for immunization by administration of the DNA directly, for example, by injection for genetic immunization or by constructing a live vector such as Salmonella, adenovirus, poxvirus, vaccinia or poliovirus. A discussion of some live vectors that have been used to carry heterologous antigens to the immune system are discussed in, for example, O'Hagan (ref 5). Processes for the direct injection of DNA into test subjects for genetic immunization are described in, for example, Ulmer et al. (ref. 6).

Immunogenicity can be significantly improved if the antigens are co-administered with adjuvants, commonly used as an 0.05 to 1.0 percent solution in phosphate—buffered saline. Adjuvants enhance the immunogenicity of an antigen but are not necessarily immunogenic themselves. Adjuvants may act by retaining the antigen locally near the site of administration to produce a depot effect facilitating a slow, sustained release of antigen to cells of the immune system. Adjuvants can also attract cells of the immune system to an antigen depot and stimulate such cells to elicit immune responses.

Immunostimulatory agents or adjuvants have been used for many years to improve the host immune responses to, for example, vaccines. Intrinsic adjuvants, such as lipopolysaccharides, normally are the components of the killed or attenuated bacteria used as vaccines. Extrinsic adjuvants are immunomodulators which are typically non-covalently linked to antigens and are formulated to enhance the host immune responses. Thus, adjuvants have been identified that enhance the immune response to antigens delivered parenterally. Some of these adjuvants are toxic, however, and can cause undesirable side-effects, making them unsuitable for use in humans and many animals. Indeed, only aluminum hydroxide and aluminum phosphate (collectively commonly referred to as alum) are routinely used as adjuvants in human and veterinary vaccines. The efficacy of alum in increasing antibody responses to diphtheria and tetanus toxoids is well established and an HBsAg vaccine has been adjuvanted with alum.

A wide range of extrinsic adjuvants can provoke potent immune responses to antigens. These include saponins complexed to membrane protein antigens (immune stimulating complexes), pluronic polymers with mineral oil, killed mycobacteria and mineral oil, Freund's complete adjuvant, bacterial products, such as muramyl dipeptide (MDP) and lipopolysaccharide (LPS), as well as lipid A, and liposomes. To efficiently induce humoral immune responses and cell-mediated immunity, immunogens are often emulsified in adjuvants.

2. Use of Sequences as Hybridization Probes

The nucleotide sequences of the present invention, encoding a mycobacterial protein associated with cell binding and cell entry, now allow for the identification and cloning of the corresponding genes from any species of Mycobacterium.

The nucleotide sequences of the present invention are useful for their ability to selectively form duplex molecules with complementary stretches of other genes encoding a mycobacterial protein associated with cell binding and cell entry. Depending on the application, a variety of hybridization conditions may be employed to achieve varying degrees of selectivity of the probe toward these other genes. For a high degree of selectivity, relatively stringent conditions are used to form the duplexes, such as low salt and/or high temperature conditions, such as provided by 0.02 M to 0.15 M NaCl at temperatures of between about 50° C. to 70° C. For some applications, less stringent hybridization conditions are required such as 0.15 M to 0.9 M salt, at temperatures ranging from between about 30° C. to about 55° C. Hybridization conditions can also be rendered more stringent by the addition of formamide, to destabilize the hybrid duplex. Thus, particular hybridization conditions can be readily manipulated, and will generally be a method of choice depending on the desired results. In general, convenient hybridization temperatures in the presence of 50% formamide are: 42° C. for a probe which is 95 to 100% homologous to the target fragment, 37° C. for 90 to 95% homology and 32° C. for 85 to 90% homology.

In a clinical diagnostic embodiment, the nucleic acid sequences of the genes of the present invention may be used in combination with an appropriate indicator, such as a label, for determining hybridization. A wide variety of appropriate indicators are known in the art, including radioactive, enzymatic or other ligands, such as avidin/biotin and digoxigenin-labelling, which are capable of providing a detectable signal. In some diagnostic embodiments, an enzyme tag such as urease, alkaline phosphatase or peroxidase may be used. In the case of enzyme tags, calorimetric indicator substrates are known which can be employed to provide a reaction visible to the human eye or spectrophotometrically, to identify specific hybridization with samples containing gene sequences.

The nucleic acid sequences of the present invention are useful as hybridization probes in solution hybridizations and in embodiments employing solid-phase procedures. In embodiments involving solid-phase procedures, the test DNA (or RNA) from samples, such as clinical samples, including exudates, body fluids (e.g., serum, sputum, bronchoalveolar lavage fluid) or even tissues, is adsorbed or otherwise affixed to a selected matrix or surface. The fixed, single-stranded nucleic acid is then subjected to specific hybridization with selected probes comprising the nucleic acid sequences of the genes of the present invention under desired conditions. The selected conditions will depend on the particular circumstances based on the particular criteria required depending on, for example, the G+C contents, type of target nucleic acid, source of nucleic acid, size of hybridization probe etc. Following washing of the hybridization surface so as to remove non-specifically bound probe molecules, specific hybridization is detected, or even quantified, by means of the label or indicator. It is preferred to select nucleic acid sequence portions which are conserved among various species of Mycobacterium. The selected probe may be at least 18 bp and may be in the range of about 30 to about 90 bp, or greater.

3. Expression of the Genes

Vectors containing replicon and control sequences which are derived from species compatible with the host cell may be used for the expression of the genes encoding a mycobacterial protein associated with cell binding and cell entry. The vector ordinarily carries a replication site, as well as marking sequences which are capable of providing phenotypic selection in transformed cells. For example, *E. coli* may be transformed using plasmid pBR322 which contains genes for ampicillin and tetracycline resistance and thus provides easy means for identifying transformed cells. The pBR322 plasmid, or other microbial plasmid or phage, must also contain, or be modified to contain, promoters which can be used by the host cell for expression.

In addition, phage vectors containing replicon and control sequences that are compatible with the host can be used as a transforming vector in connection with these hosts. For example, the phage in lambda GEM™-11 may be utilized in making recombinant phage vectors which can be used to transform host cells, such as *E. coli* K12 strain LE392.

Promoters commonly used in recombinant DNA construction include the β-lactamase (penicillinase) and lactose promoter systems and other microbial promoters, such as the T7 RNA polymerase promoter system as described in U.S. Pat. No. 4,952,496. Details concerning the nucleotide sequences of promoters are known, enabling a skilled worker to ligate them functionally with genes. The particular promoter used will generally be a matter of choice depending upon the desired results. Hosts that are appropriate for expression of the genes provided herein may include bacteria such as *E. coli,* Bordetella, Bacillus species, Haemophilus, fungi, yeast, mammalian cells or the baculovirus expression system may be used.

In accordance with this invention, it is preferred to make the mycobacterial protein associated with cell binding and cell entry by recombinant methods, particularly when the naturally occurring protein as purified from a culture of a species of Mycobacterium may include trace amounts of toxic materials or other contaminants. This problem can be avoided by using recombinantly produced protein in heterologous systems which can be isolated from the host in a manner to minimize contaminants. Particularly desirable hosts for expression in this regard include Gram positive bacteria which do not have LPS and are, therefore, endotoxin free. Such hosts include species of Bacillus and may be particularly useful for the production of non-pyrogenic mycobacterial protein associated with cell entry and cell binding and having a molecular weight of between about 45,000 to about 60,000.

Biological Deposits

A vector that contains the gene encoding a mycobacterial protein associated with cell binding and cell entry and having a molecular weight of between about 45,000 and about 60,000 from the *M. bovis* strain BCG that is described and referred to herein has been deposited with the American Type Culture Collection (ATCC) located at 12301 Parklawn Drive, Rockville, Md. 20852, USA, pursuant to the Budapest Treaty and prior to the filing of this application. Samples of the deposited vectors will become available to the public upon grant of a patent based upon this United States patent application and all restrictions on access to the deposit will be removed at that time. The invention described and claimed herein is not to be limited in scope by the biological material deposited, since the deposited embodiment is intended only as an illustration of the invention. Any equivalent or similar vectors that encode similar or equivalent antigens as described in this application are within the scope of the invention.

Deposit Summary

| Deposit | ATCC Designation | Date Deposited |
| --- | --- | --- |
| Plasmid pBCGcepX | 97511 | April 11, 1996 |

EXAMPLES

The above disclosure generally describes the present invention. A more complete understanding can be obtained by reference to the following specific Examples. These Examples are described solely for purposes of illustration and are not intended to limit the scope of the invention. Changes in form and substitution of equivalents are contemplated as circumstances may suggest or render expedient. Although specific terms have been employed herein, such terms are intended in a descriptive sense and not for purposes of limitation.

Example 1

This Example illustrates recombinant DNA methods.

Restriction enzymes and cloning vectors were obtained from several sources including New England Biolabs, Gibco/BRL Life Technologies, Boehringer Mannheim and Stratagene. Reagents used in DNA isolation protocols were purchased from Sigma Biochemical. Most recombinant DNA manipulations were performed using standard protocols (ref. 7). Sequencing was performed on an Applied Biosystems automated sequencer (370A) using dideoxy terminator chemistry with reagents in kit form and protocols supplied by the manufacturer. The synthesis of oligonucleotides used as primers was performed using an Applied Biosystems (380B) synthesizer. The synthetic polynucleotides were purified on OPC cartridges supplied by Applied Biosystems according to the manufacturers protocol.

*M. bovis* BCG DNA was isolated using a modification of a technique described in the literature (ref. 8). A starter culture of *M. bovis* BCG (Connaught) at $A_{600}$ of 3.4 (10 mL) was inoculated into 100 mL of Middlebrook 7H9 media (Difco Labs) supplemented with ADC enrichment (BBL, to 10%) and Tween 80 (Sigma, 0.05%). This culture was incubated for 14 days at 37° C. in roller bottles, subsequently, 50 mL of culture was centrifuged (6,000 g for 10 min.) to pellet the cells. The pellet was resuspended 1 mL of TE buffer (10 mM Tris-HCl, pH7.5 and 1 mM EDTA) containing 200 µg/mL of Proteinase K (Gibco/BRL) and 10 mg/mL of hen egg white lysozyme (Sigma). The suspension was incubated at 37° C. for 60 min., spun down in a centrifuge (12,000 g for 1 min.) and the pellet resuspended in 1 ml of DNAzol™ reagent with vortexing. The suspension was transferred to a 2 mL screw capped tube filled to a quarter of its volume with glass beads (106 µm or finer) and vortexed vigorously for 10 min. The beads were then allowed to settle and the supernatant transferred to a fresh tube which was centrifuged for 10 minutes at room temperature. The resultant lysate was transferred to a new tube and 0.5 mL of 100% ethanol was added. The tube was inverted several times to mix and the mixture incubated at room temperature for 3 to 5 min. The tube was spun in a centrifuge (at 1,000 g for 2 min.) to pellet the DNA, the supernatant discarded, the pellet washed twice with 1 mL of 95% ethanol and then air dried at room temperature for 15 min. Finally, the pellet was dissolved in 0.2 mL of TE buffer and the quantity of DNA estimated by measuring the optical density at 260 nm in a spectrophotometer. This protocol yields approximately 80 µg of DNA.

Example 2

This Example describes the PCR amplification of the *Mycobacterium bovis* BCG gene encoding a mycobacterial protein associated with cell binding and cell entry.

PCR amplification reactions were carried out on *M. bovis* BCG chromosomal DNA and pZX7 plasmid (pBluescript(+) from Stratagene) containing the 1535 bp insert from *Mycobacterium tuberculosis* H37Ra supplied by Dr. Riley (ref. 4). The primers and their sequences used in PCR amplifications are listed in Table 1. The corresponding positions of these primers relative to the ORF1 encoding the mce gene of *Mycobacterium tuberculosis* (as published in ref. 4) are illustrated in FIG. 1 as a thick filled line. The amplifications were carried out using the "Hot Start procedure". Essentially a 40 µL reaction mix containing dNTP's (0.2 mM in 100 µL final volume), buffer and a pair of primers (100 pM of each) was prepared in thin walled eppendorf tubes. To each tube a bead of wax (PCRGem™, 100, Perkin-Elmer) was added and the tube heated to 70° C. for 5 min. Subsequently, the tube was cooled to room temperature for 5 min. and a reaction mix (60 µL) containing buffer (supplied by manufacturer as a 10×concentration), 1 unit of enzyme (Amplitaq™ or Taq'plus') and DNA template (*M. bovis* BCG chromosomal DNA 1 µg or 50 ng of plasmid) were added. The tubes where then placed in a Perkin-Elmer Cetus thermal cycler and a cycling sequence started based on the following parameters:

Step 1: 93° C. for 1 minute;
Step 2: 93° C. for 1 minute, 60° C. for 1 minute; 72° C. for 2 minutes; repeated for 10 cycles;
Step 3: 93° C. for 1 minute; 60° C. for 1 minute; 72° C. for 2 minutes (auto ext. 5 seconds); repeated for 20 cycles.
Step 4: 72° C. for 10 minutes; and
Step 5: Maintain at 4° C.

The tubes were stored at 4° C. aliquots of 10 µL were run on a 0.8% agarose gel, the bands visualized and photographed.

Example 3

This Example describes the construction of *Mycobacterium bovis* BCG libraries.

Restriction enzyme digestion of *M. bovis* BCG DNA and subsequent Southern blot using a PCR amplified product (primer pairs 4414/4448; Lane 2; panel A, FIG. 2) as a probe, indicated the presence of the gene on 1.5 kb and 5 kb fragments of Sal I and Xho I digests (FIG. 3). The corresponding bands were cut out and ligated into suitably digested pUC18 and pBluescript II sk(+) plasmids respectively. The libraries obtained after transformation of these plasmids into competent *E. coli* cells were probed for the gene by hybridization and two positive clones identified. These were grown, plasmid isolated and analyzed to yield two clones. Plasmid pBCGcepX contained an approximately 5 kb DNA insert containing the putative gene and another plasmid pBCGcepS containing a 1.5 kb Sal I insert which also hybridized to the mce gene specific probe. (FIG. 4, dark filled arcs in panels A and B).

For Southern blot analysis an aliquot of *M. bovis* BCG DNA (1.2 µg) was digested with restriction endonucleases Eco R I, Hind III, Nde I, Bgl II, Dra III, Sac I, Sal I and Xho I (using 5 to 10 units each). The digestion was carried out in a total volume of 20 µL for 4 hours using standard buffer and conditions. The digests were mixed with loading buffer and run on a 0.8% agarose gel (FIG. 2, panel A). The gel was transferred to a nylon membrane using standard reagents and protocols and the DNA fixed to the membrane. The amplification product of a PCR reaction on BCG DNA using primers 4414 and 4448 (Lane 4, panel A, FIG. 1) was isolated by excising the corresponding band from the gel and extracting the DNA. The isolated DNA was labelled with 32p using the "Random priming system I" kit (New England Biolabs) for use as a hybridization probe. The membrane was prehybridized, hybridized with the labelled probe overnight at 55° C. and subsequently washed. The blot was exposed to film overnight at room temperature and the autoradiograph developed (FIG. 2: panel B).

*M. bovis* BCG DNA was digested with Sal I and Xho I restriction enzymes and the digests run out on a 0.8% agarose gel. Bands of 1.5 kb and 5 kb (panel B, FIG. 2) were excised. The DNA was isolated from these agarose slices and ligated to Sal I digested pUC18 or Xho I digested pBluescript II sk(+) using T4 DNA ligase. The ligation reactions were used to transform competent *E. coli* K12 strain (TG1) cells and the colonies plated out on LB agar containing ampicillin. These were transferred to nitrocellulose membranes (Schleicher & Schuell) and probed with the labelled polynucleotide used in the above Southern blotting procedure. Positive colonies were identified, isolated, grown up and purified plasmid analyzed for inserted DNA following Sal I or Xho I digestion. Two clones, one containing an approximately 5 kb Xho I insert (pBCGcepX) and another containing a 1.5 kb Sal I (pBCGsepS) insert were identified. These clones were grown up, the plasmid isolated using a kit for high grade plasmid purification (Qiagen) and the genes sequenced.

Example 4

This Example describes the specific identification of *M. tuberculosis* from other pathogens by Southern hybridization using the gene encoding the mycobacterial protein associated with cell binding and cell entry.

The isolated nucleic acid molecule encoding a mycobacterial protein associated with cell binding and cell entry and having a molecular weight of about 45 to about 60 kDa is useful in a diagnostic embodiment for specifically distinguishing mycobacteria from other pathogens.

Chromosomal DNA (1 μg) from *M. bovis* BCG (Connaught); *M. tuberculosis* clinical isolates TB188, TB421 and TB458 from U.S.A., Uganda and Brazil respectively, and *B. pertussis, B. catarrhalis, P. auregenosa* and *H. influenzae* (Eagan strain) were digested with Xho I. The digests together with undigested chromosomal BCG DNA were electrophoresed on a 0.8% agarose gel and blotted onto a nylon membrane. The 5 kb XhoI insert of plasmid pBCGcepX was isolated labelled with $^{32}$P and used as a probe for the Southern blot. The blot was washed and exposed to film. The gel and auto radiograph after a 48 hour exposure are illustrated in FIG. 11.

SUMMARY OF THE DISCLOSURE

In summary of this disclosure, the present invention provides isolated nucleic acid molecules which encode a protein of a Mycobacterium strain associated with cell binding and cell entry and having a molecular weight of about 45 to about 60 kDa as well as the isolated and purified protein encoded thereby. Modifications are possible within the scope of this invention.

TABLE 1

Sequence of PCR Primers

| PRIMER # | SEQUENCE (5'-3') | SEQ. ID No. |
|---|---|---|
| 4676 | CCGCGGATCCGTGAACGCCGACATCAAGGCGACC | 4 |
| 4677 | CATGGATCCCTATGCGGCAGCCCCGCGGTCAGG | 5 |
| 4414 | GTATGTGTCGTTGACCACGCC | 6 |
| 4417 | ACTCCGGGCCTATGCGGCAGC | 7 |
| 4447 | GCGTGCATGCGTTCGGCGTGGACCGC | 8 |
| 4448 | TCAGGTCGATCGGCATCGTAGAAG | 9 |
| 4812 | CGAGCAGCGCAACGACGATGC | 10 |
| 4865 | CCGTTGCTGATGTGCGCGAG | 11 |
| 4879 | CATGGTCAGCCACTGCTACTAC | 12 |
| 4880 | GAACCACTCCGGGCCTATGCGGC | 13 |
| 4881 | GATCTCTGAGTTCGTCCTCAGCGAG | 14 |
| 4882 | CGACGGTTCCAGTGATTTTCATGG | 15 |
| 4415 | CCGTATCTGCAGCGGGGGGTC | 16 |

TABLE 2

Amino Acid Composition of the Mycobacterial
Cell Binding and Cell Entry Associated Protein
of *M. bovis* BCG

| Amino Acids | Number of Residues | Percentage (MW) |
|---|---|---|
| L - Leucine | 53 | 10.7 |
| R - Arginine | 32 | 8.9 |
| T - Threonine | 45 | 8.1 |
| A - Alanine | 60 | 7.6 |
| V - Valine | 40 | 7.1 |
| S - Serine | 43 | 6.7 |
| P - Proline | 38

What we claim is:

1. An isolated nucleic acid fragment comprising a nucleic acid sequence that has at least 85% homology as compared to the full length of SEQ ID NO: 2 and encodes a mycobacterial protein associated with cell binding and cell entry having a molecular weight of about 45 to about 60 kDa.

2. The isolated nucleic acid fragment as claimed in claim 1 which is amplificable by polymerase chain reaction (PCR) by a pair of primers consisting of the sequences of primers 4879 (SEQ ID NO:12) and 4882 (SEQ ID NO: 15); or 4879 (SEQ ID NO: 12) and 4865 (SEQ ID NO: 11); or 4879 (SEQ ID NO: 12) and 4812 (SEQ ID NO: 10).

3. The nucleic acid fragment of claim 9 from a Mycobacterium strain of *Mycobacterium tuberculosis*.

4. The nucleic acid fragment of claim 2 from a Mycobacterium strain of *Mycobacterium bovis*.

5. A vector for transformation of a host comprising the nucleic acid fragment of claim 2.

6. The vector of claim 5 further comprising DNA sequences for expression of said protein in said host.

7. An isolated host cell transformed to contain an expression vector as claimed in claim 6.

8. A method of producing a substantially pure recombinant mycobacterial protein associated with cell binding and cell entry and having a molecular weight between about 45 kDa and 60 kDa, which comprises:

transforming a host with a vector as claimed in claim 6;

growing the transformed host to express the protein, and isolating and purifying the protein free from other proteinaceous and cellular material.

9. An immunogenic composition, comprising at least one nucleic acid fragment as claimed in claim 2 as an active component thereof, and a pharmaceutically acceptable carrier.

10. A method of generating an immune response in a host, which comprises administering to the host an immunoeffective amount of the immunogenic composition of claim 9.

* * * * *

SEQUENCE LISTING (1) GENERAL INFORMATION:

(iii) NUMBER OF SEQUENCES: 17

(2) INFORMATION FOR SEQ ID NO:1:

(i) SEQUENCE CHARACTERISTICS:
       (A) LENGTH: 4739 base pairs
       (B) TYPE: nucleic acid
       (C) STRANDEDNESS: single
       (D) TOPOLOGY: linear (xi) SEQUENCE DESCRIPTION: SEQ ID NO:1:

```
ATCGTGGACG CTCTGCCCCG CAACCCCGCG GGGAAGGTGC TCAAGACTGA ACTGCGATTG      60

CGCTACGGCG CCTGTGTGAA TGTTGAAAGA CGTTCTGCAT CAGCTGGTTT CACGGAGAGA     120

AGGGAAAATC GACAGAAATT GTAACGTTTG CCCGCTATTG ACGAAGGGTT AAATGTGCGG     180

ATGCCTTACA CTCCTGGCTG GCCATCGGGT AGATTCCTGT GGTCTCCGTT ACTCCCTGTG     240

AGTAACGAGG TGGCGGTCAC ACACCAAGGG TCGGGGCAAG GAAGAAGCGT GCGACATGAT     300

GCGCCGCGGC GCCGCGATAC CCAGGTCGGC GGCTTGAGGG AGCCGCGGTG ACGACGTCGA     360

CAACGCTTGG CGGTTACGTC CGCGACCAAC TGCAAACCCC GCTGACCCTC GTCGGTGGAT     420

TCTTTCGCAT GTGTGTGCTG ACTGGAAAGG CGCTGTTTCG CTGGCCGTTC CAGTGGCGCG     480

AGTTCATTCT GCAGTGCTGG TTCATCATGC GGGTCGGATT TTTACCGACG ATCATGGTCT     540

CGATACCGCT GACGGTGCTG TTGATCTTCA CGCTCAATAT TCTGCTGGCC CAGTTCGGCG     600

CGGCAGACAT CTCCGGTTCC GGCGCGGCGA TCGGCGCGGT CACCCAGCTT GGCCCGCTGA     660

CAACGGTGCT GGTGGTCGCC GGCGCCGGAT CCACGGCCAT CTGCGCCGAC CTGGGTGCCC     720

GCACCATCCG CGAGGAAATC GACGCGATGG AGGTGCTGGG CATCGATCCC ATCCACCGTC     780

TGGTGGTGCC GCGGGTGCTC GCCTCGATGC TGGTCGCCAC GCTGCTCAAC GGCTTGGTGA     840

TCACCGTCGG CCTGGTCGGT GGCTTTCTCT TCGGTGTCTA TCTGCAGAAC GTTTCGGGCG     900

GCGCCTACCT TGCCACGCTG ACCTTGATCA CCGGCCTGCC CGAGGTGGTC ATCGCAACCA     960

TCAAAGCCGC AACGTTCGGC CTGATCGCGG GCCTTGTCGG CTGCTATCGG GGGCTGACCG    1020

TCCGTGGCGG TTCCAAGGGT CTTGGCACCG CCGTCAACGA GACCGTGGTG CTGTGTGTGA    1080

TTGCCCTGTT CGCCGTCAAC GTGATCTTGA CGACCATCGG TGTGCGATTC GGGACGGGGC    1140

GCTGACATGT CGACCGCTGC TGTGCTGCGC GCCCGCTTCC CGCGGGCGGT CGCCAACCTT    1200

CGTCAATATG GAGGTGCGGC GGCCCGTGGA TTGGACGAGG CCGGCCAGCT CACCTGGTTC    1260

GCTTTGACCA GCATCGGGCA GATCGCGCAC GCGCTGCGCT ACTACCGCAA GGAGACGCTG    1320

CGGCTGATCG CCCAGATCGG CATGGGTACC GGCGCGATGG CCGTCGTCGG CGGCACGGTC    1380

GCCATCGTTG GCTTTGTCAC GCTGTCCGGC AGCTCGCTGG TCGCAATCCA GGGCTTCGCG    1440

TCGCTGGGCA ACATCGGTGT CGAGGCGTTC ACCGGGTTCT TCGCCGCACT GATCAACGTG    1500

CGCATCGCCG GCCCAGTTGT CACGGGTGTC GCCCTGGCGG CCACGGTCGG TGCGGGTGCT    1560

ACGGCCGAGC TGGGCGCGAT GCGGATCAGC GAGGAGATCG ATGCCCTGGA AGTGATGGGC    1620

ATAAAGTCGA TCTCGTTTCT GGCCTCCACC CGGATCATGG CCGGGCTGGT GGTGATCATC    1680

CCGCTGTACG CGTTGGCGAT GATTATGTCG TTCCTGTCCC CGCAGATCAC CACCACGGTG    1740

CTCTACGGGC AGTCGAACGG CACCTACGAG CATTACTTTC AAACGTTCCT GCGTCCCGAC    1800

GATGTCTTTT GGTCCTTCTT GGAGGCCCTC ATCATCACTG CGATCGTCAT GGTCAGCCAC    1860
```

```
TGCTACTACG GGTACGCCGC CGGTGGAGGC CCCGTCGGTG TCGGCGAGGC CGTCGGCCGA    1920

TCGATGCGTT TCTCGTTGGT CTCGGTGCAG GTCGTTGTCC TGTTTGCAGC GTTGGCGCTC    1980

TACGGTGTCG ACCCGAACTT CAATCTCACG GTGTAGCCGC ATGACGACGC CGGGGAAGCT    2040

GAACAAGGCG CGAGTGCCGC CCTACAAGAC GGCGGGTTTG GGTCTAGTGC TGGTCTTCGC    2100

GCTCGTAGTT GCCTTGGTAT ACCTGCAGTT TCGCGGGGAG TTCACGCCCA AGACGCAGTT    2160

GACGATGCTG TCCGCTCGTG CGGGTTTGGT GATGGATCCC GGGTCGAAGG TCACCTATAA    2220

CGGGGTGGAG ATCGGGCGGG TAGACACCAT CTCGGAGGTC ACACGTGACG GCGAGTCGGC    2280

GGCCAAGTTC ATCTTGGATG TGGATCCGCG TTACATCCAC CTGATTCCGG CAAATGTGAA    2340

CGCCGACATC AAGGCGACCA CGGTGTTCGG CGGTAAGTAT GTGTCGTTGA CCACGCCGAA    2400

AAACCCGACA AGAGGCGGA TAACGCCAAA AGACGTCATC GACGTACGGT CGGTGACCAC    2460

CGAGATCAAC ACGTTGTTCC AGACGCTCAC CTCGATCGCC GAGAAGGTGG ATCCGGTCAA    2520

GCTGAACCTG ACCCTGAGCG CGGCCGCGGA GGCGTTGACC GGGCTGGGCG ATAAGTTCGG    2580

CGAGTCGATC GTCAACGCCA ACACCGTTCT GGATGACCTC AATTCGCGGA TGCCGCAGTC    2640

GCGCCACGAC ATTCAGCAAT TGGCGGCTCT GGGCGACGTC TACGCCGACG CGGCGCCGGA    2700

CCTGTTCGAC TTTCTCGACA GTTCGGTGAC CACCGCCCGC ACCATCAATG CCCAGCAAGC    2760

GGAACTGGAT TCGGCGCTGT TGGCGGCGGC CGGGTTCGGC AACACCACAG CCGATGTCTT    2820

CGACCGCGGC GGGCCGTATC TGCAGCGGGG GGTCGCCGAC CTGGTCCCCA CCGCCACCCT    2880

GCTCGACACT TATAGCCCGG AACTGTTCTG CACGATCCGC AACTTCTACG ATGCCGATCC    2940

GCTCGCTAAA GCGGCGGCCG GTGGCGGTAA CGGCTACTCG CTGAGGACGA ACTCAGAGAT    3000

CCTATCCGGG ATAGGTATCT CCTTGTTGTC TCCCCTGGCG TTAGCCACCA ATGGGGCGGC    3060

AATCGGAATC GGACTGGTAG CCGGATTGAT AGCGTCGCCC CTCGCGGTGG CCGCAAATCT    3120

AGCGGGAGCC CTACCCGGAA TCGTTGGCGG CGCGCCCAAT CCCTATACCT ATCCGGAGAA    3180

TCTGCCGCGG GTGAACGCTC GCGGTGGCCC GGGGGGCGCC CCCGGTTGCT GGCAGCCGAT    3240

CACCCGGGAT CTGTGGCCAG CGCCGTATCT GGTGATGGAC ACCGGTGCCA GCCTCGCCCC    3300

GTACAACCAC ATGGAGGTTG GCTCGCCTTA TGCAGTCGAG TACGTCTGGG GCCGTCAGGT    3360

AGGGGATAAC ACGATCAACC CATGAAAATC ACTGGAACCG TCGTCAAACT CGGCATCGTC    3420

TCGGTGGTGC TGCTGTTCTT CACGGTGATG ATCATCGTGA TTTTCGGTCA GATGCGCTTC    3480

GACCGGACTA ATGGCTATAC CGCGGAGTTC AGCAATGTCA GCGGGCTGCG CCAAGGCCAG    3540

TTTGTCCGTG CTTCGGGGGT AGAGATCGGC AAGGTCAAAG CACTACACCT GGTCGACGGT    3600

GGCCGTCGGG TTCGGGTGGA GTTCAATATC GATCGTTCGG TGCCGTTGTA TCAGTCCACG    3660

ACCGCCCAGA TCCGCTATTC CGACCTGATC GGTAACCGGT ACGTGGAGCT CAAACGGGGT    3720

GAGGGCAAGG GGGCCAACGA TCTGCTGCCG CCAGGTGGAC TCATCCCATT GTCCCGCACG    3780

TCACCGGCCT TGGATCTGGA CGCGTTGATC GGTGGTTTCA AGCCGGTGTT TCGGGCGTTG    3840

GATCCCGCGA AGGTGAACAA CATCGCCAAC GCGCTCATCA CCGTCTTCCA GGGGCAAGGT    3900

GGCACCATAA ACGACACCCT CGACCAGACC GCGCAACTGA CCAGCCAGAT CGCGGAGCGC    3960

GATCAGGCGA TCGGTGAGGT TGTCAAGAAC CTGAACATCG TGCTGGACAC CACGGTCAAG    4020

CATCGAAAAG AGTTCGACGA GACGGTCAAT AACTTGGAGA ATCTGATCAC TGGGCTGAGG    4080

AACCACTCCG ACCAGTTGGC CGGCGGCCTC GCGCACATCA GCAACGGCGC CGGCACGGTG    4140

GCCGACCTGC TTGCCGAGAA TCGCACGTTG GTGCGCAAGG CCGTCAGCTA CCTGGACGCT    4200
```

-continued

```
ATTCAGCAAC CGGTCATCGA CCAGCGCGTC GAGTTGGACG ACCTGCTCCA CAAGACGCCG    4260

ACCGCGTTGA CGGCGCTCGG ACGCGCCAAC GGAACCTACG GCGATTTCCA GAACTTCTAC    4320

CTCTGCGACC TCCAGATCAA GTGGAACGGA TTCCAAGCCG GAGGGCCGGT CCGCACGGTG    4380

AAGCTCTTTA GCCAGCCGAC GGGTAGGTGC ACGCCGCAAT GAGAACGCTG GAACCACCCA    4440

ACCGAATGCG AATTGGGCTC ATGGGCATCG TCGTTGCGCT GCTCGTTGTC GCTGTGGGCC    4500

AAAGCTTTAC CAGTGTTCCC ATGCTATTCG CAAAGCCGAG CTACTACGGC CAGTTCACCG    4560

ACTCCGGCGG ACTGCACAAG GGCGACAGGG TACGCATCGC CGGCTTGGGA GTGGGCACCG    4620

TGGAGGGGCT CAAGATCGAC GGCGACCACA TCGTGGTCAA GTTCTCCATC GGCACCAACA    4680

CCATCGGCAC CGAGAGCCGC CTAGCCATCC GCACCGACAC CATCCTGGGT AGGAAAGTG     4739
```

(2) INFORMATION FOR SEQ ID NO:2:

(i) SEQUENCE CHARACTERISTICS:
        (A) LENGTH: 1584 base pairs
        (B) TYPE: nucleic acid
        (C) STRANDEDNESS: single
        (D) TOPOLOGY: linear (xi) SEQUENCE DESCRIPTION: SEQ ID NO:2:

```
ATGTCTTTTG GTCCTTCTTG GAGGCCCTCA TCATCACTGC GATCGTCATG GTCAGCCACT      60

GCTACTACGG GTACGCCGCC GGTGGAGGCC CCGTCGGTGT CGGCGAGGCC GTCGGCCGAT     120

CGATGCGTTT CTCGTTGGTC TCGGTGCAGG TCGTTGTCCT GTTTGCAGCG TTGGCGCTCT     180

ACGGTGTCGA CCCGAACTTC AATCTCACGG TGTAGCCGCA TGACGACGCC GGGGAAGCTG     240

AACAAGGCGC GAGTGCCGCC CTACAAGACG GCGGGTTTGG GTCTAGTGCT GGTCTTCGCG     300

CTCGTAGTTG CCTTGGTATA CCTGCAGTTT CGCGGGAGT TCACGCCCAA GACGCAGTTG      360

ACGATGCTGT CCGCTCGTGC GGGTTTGGTG ATGGATCCCG GGTCGAAGGT CACCTATAAC     420

GGGGTGGAGA TCGGGCGGGT AGACACCATC TCGGAGGTCA CACGTGACGG CGACTCGGCG     480

GCCAAGTTCA TCTTGGATGT GGATCCGCGT TACATCCACC TGATTCCGGC AAATGTGAAC     540

GCCGACATCA AGGCGACCAC GGTGTTCGGC GGTAAGTATG TGTCGTTGAC CACGCCGAAA     600

AACCCGACAA AGAGGCGGAT AACGCCAAAA GACGTCATCG ACGTACGGTC GGTGACCACC     660

GAGATCAACA CGTTGTTCCA GACGCTCACC TCGATCGCCG AGAAGGTGGA TCCGGTCAAG     720

CTGAACCTGA CCCTGAGCGC GGCCGCGGAG GCGTTGACCG GCTGGGCGA TAAGTTCGGC      780

GAGTCGATCG TCAACGCCAA CACCGTTCTG GATGACCTCA ATTCGCGGAT GCCGCAGTCG     840

CGCCACGACA TTCAGCAATT GGCGGCTCTG GGCGACGTCT ACGCCGACGC GGCGCCGGAC     900

CTGTTCGACT TTCTCGACAG TTCGGTGACC ACCGCCCGCA CCATCAATGC CCAGCAAGCG     960

GAACTGGATT CGGCGCTGTT GGCGGCGGCC GGGTTCGGCA ACACCACAGC CGATGTCTTC    1020

GACCGCGGCG GGCCGTATCT GCAGCGGGGG GTCGCCGACC TGGTCCCCAC CGCCACCCTG    1080

CTCGACACTT ATAGCCCGGA ACTGTTCTGC ACGATCCGCA ACTTCTACGA TGCCGATCCG    1140

CTCGCTAAAG CGGCGGCCGG TGGCGGTAAC GGCTACTCGC TGAGGACGAA CTCAGAGATC    1200

CTATCCGGGA TAGGTATCTC CTTGTTGTCT CCCCTGGCGT TAGCCACCAA TGGGGCGGCA    1260

ATCGGAATCG GACTGGTAGC CGGATTGATA GCGTCGCCCC TCGCGGTGGC CGCAAATCTA    1320

GCGGGAGCCC TACCCGGAAT CGTTGGCGGC GCGCCCAATC CCTATACCTA TCCGGAGAAT    1380

CTGCCGCGGG TGAACGCTCG CGGTGGCCCG GGGGCGCCCC CCGGTTGCTG GCAGCCGATC    1440

ACCCGGGATC TGTGGCCAGC GCCGTATCTG GTGATGGACA CCGGTGCCAG CCTCGCCCCG    1500
```

```
TACAACCACA TGGAGGTTGG CTCGCCTTAT GCAGTCGAGT ACGTCTGGGG CCGTCAGGTA    1560

GGGGATAACA CGATCAACCC ATGA                                          1584
```

(2) INFORMATION FOR SEQ ID NO:3:

(i) SEQUENCE CHARACTERISTICS:
        (A) LENGTH: 527 amino acids
        (B) TYPE: amino acid
        (D) TOPOLOGY: linear (ii) MOLECULE TYPE: protein (xi) SEQUENCE DESCRIPTION: SEQ ID NO:3:

```
Met Ser Phe Gly Pro Ser Trp Arg Pro Ser Ser Leu Arg Ser Ser
 1               5                  10                  15

Trp Ser Ala Thr Ala Thr Thr Gly Thr Pro Pro Val Glu Ala Pro Ser
                20                  25                  30

Val Ser Ala Arg Pro Ser Ala Asp Arg Cys Val Ser Arg Trp Ser Arg
                35                  40                  45

Cys Arg Ser Leu Ser Cys Leu Gln Arg Trp Arg Ser Thr Val Ser Thr
            50                  55                  60

Arg Thr Ser Ile Ser Arg Cys Ser Arg Met Thr Thr Pro Gly Lys Leu
 65                  70                  75                  80

Asn Lys Ala Arg Val Pro Pro Tyr Lys Thr Ala Gly Leu Gly Leu Val
                85                  90                  95

Leu Val Phe Ala Leu Val Val Ala Leu Val Tyr Leu Gln Phe Arg Gly
                100                 105                 110

Glu Phe Thr Pro Lys Thr Gln Leu Thr Met Leu Ser Ala Arg Ala Gly
                115                 120                 125

Leu Val Met Asp Pro Gly Ser Lys Val Thr Tyr Asn Gly Val Glu Ile
            130                 135                 140

Gly Arg Val Asp Thr Ile Ser Glu Val Thr Arg Asp Gly Asp Ser Ala
145                 150                 155                 160

Ala Lys Phe Ile Leu Asp Val Asp Pro Arg Tyr Ile His Leu Ile Pro
                165                 170                 175

Ala Asn Val Asn Ala Asp Ile Lys Ala Thr Val Phe Gly Gly Lys
                180                 185                 190

Tyr Val Ser Leu Thr Thr Pro Lys Asn Pro Thr Lys Arg Arg Ile Thr
                195                 200                 205

Pro Lys Asp Val Ile Asp Val Arg Ser Val Thr Glu Ile Asn Thr
                210                 215                 220

Leu Phe Gln Thr Leu Thr Ser Ile Ala Glu Lys Val Asp Pro Val Lys
225                 230                 235                 240

Leu Asn Leu Thr Leu Ser Ala Ala Glu Ala Leu Thr Gly Leu Gly
                245                 250                 255

Asp Lys Phe Gly Glu Ser Ile Val Asn Ala Asn Thr Val Leu Asp Asp
                260                 265                 270

Leu Asn Ser Arg Met Pro Gln Ser Arg His Asp Ile Gln Gln Leu Ala
            275                 280                 285

Ala Leu Gly Asp Val Tyr Ala Asp Ala Ala Pro Asp Leu Phe Asp Phe
            290                 295                 300

Leu Asp Ser Ser Val Thr Thr Ala Arg Thr Ile Asn Ala Gln Gln Ala
305                 310                 315                 320

Glu Leu Asp Ser Ala Leu Leu Ala Ala Ala Gly Phe Gly Asn Thr Thr
                325                 330                 335
```

```
Ala Asp Val Phe Asp Arg Gly Gly Pro Tyr Leu Gln Arg Gly Val Ala
            340                 345                 350

Asp Leu Val Pro Thr Ala Thr Leu Leu Asp Thr Tyr Ser Pro Glu Leu
            355                 360                 365

Phe Cys Thr Ile Arg Asn Phe Tyr Asp Ala Asp Pro Leu Ala Lys Ala
            370                 375                 380

Ala Ala Gly Gly Gly Asn Gly Tyr Ser Leu Arg Thr Asn Ser Glu Ile
385                 390                 395                 400

Leu Ser Gly Ile Gly Ile Ser Leu Leu Ser Pro Leu Ala Leu Ala Thr
            405                 410                 415

Asn Gly Ala Ala Ile Gly Ile Gly Leu Val Ala Gly Leu Ile Ala Ser
            420                 425                 430

Pro Leu Ala Val Ala Ala Asn Leu Ala Gly Ala Leu Pro Gly Ile Val
            435                 440                 445

Gly Gly Ala Pro Asn Pro Tyr Thr Tyr Pro Glu Asn Leu Pro Arg Val
            450                 455                 460

Asn Ala Arg Gly Gly Pro Gly Gly Ala Pro Gly Cys Trp Gln Pro Ile
465                 470                 475                 480

Thr Arg Asp Leu Trp Pro Ala Pro Tyr Leu Val Met Asp Thr Gly Ala
            485                 490                 495

Ser Leu Ala Pro Tyr Asn His Met Glu Val Gly Ser Pro Tyr Ala Val
            500                 505                 510

Glu Tyr Val Trp Gly Arg Gln Val Gly Asp Asn Thr Ile Asn Pro
            515                 520                 525

(2) INFORMATION FOR SEQ ID NO:4:

(i) SEQUENCE CHARACTERISTICS:
        (A) LENGTH: 34 base pairs
        (B) TYPE: nucleic acid
        (C) STRANDEDNESS: single
        (D) TOPOLOGY: linear (xi) SEQUENCE DESCRIPTION: SEQ ID NO:4:

CCGCGGATCC GTGAACGCCG ACATCAAGGC GACC                              34

(2) INFORMATION FOR SEQ ID NO:5:

(i) SEQUENCE CHARACTERISTICS:
        (A) LENGTH: 33 base pairs
        (B) TYPE: nucleic acid
        (C) STRANDEDNESS: single
        (D) TOPOLOGY: linear (xi) SEQUENCE DESCRIPTION: SEQ ID NO:5:

CATGGATCCC TATGCGGCAG CCCCGCGGTC AGG                               33

(2) INFORMATION FOR SEQ ID NO:6:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:6:

GTATGTGTCG TTGACCACGC C                                            21

(2) INFORMATION FOR SEQ ID NO:7:

(i) SEQUENCE CHARACTERISTICS:
```

(A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:7:

ACTCCGGGCC TATGCGGCAG C                                          21

(2) INFORMATION FOR SEQ ID NO:8:

(i) SEQUENCE CHARACTERISTICS:
        (A) LENGTH: 26 base pairs
        (B) TYPE: nucleic acid
        (C) STRANDEDNESS: single
        (D) TOPOLOGY: linear (xi) SEQUENCE DESCRIPTION: SEQ ID NO:8:

GCGTGCATGC GTTCGGCGTG GACCGC                                     26

(2) INFORMATION FOR SEQ ID NO:9:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:9:

TCAGGTCGAT CGGCATCGTA GAAG                                       24

(2) INFORMATION FOR SEQ ID NO:10:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:10:

CGAGCAGCGC AACGACGATG C                                          21

(2) INFORMATION FOR SEQ ID NO:11:

(i) SEQUENCE CHARACTERISTICS:
        (A) LENGTH: 20 base pairs
        (B) TYPE: nucleic acid
        (C) STRANDEDNESS: single
        (D) TOPOLOGY: linear (xi) SEQUENCE DESCRIPTION: SEQ ID NO:11:

CCGTTGCTGA TGTGCGCGAG                                            20

(2) INFORMATION FOR SEQ ID NO:12:

(i) SEQUENCE CHARACTERISTICS:
        (A) LENGTH: 22 base pairs
        (B) TYPE: nucleic acid
        (C) STRANDEDNESS: single
        (D) TOPOLOGY: linear (xi) SEQUENCE DESCRIPTION: SEQ ID NO:12:

CATGGTCAGC CACTGCTACT AC                                         22

(2) INFORMATION FOR SEQ ID NO:13:

(i) SEQUENCE CHARACTERISTICS:
        (A) LENGTH: 23 base pairs (B) TYPE: nucleic acid
        (C) STRANDEDNESS: single
        (D) TOPOLOGY: linear (xi) SEQUENCE DESCRIPTION: SEQ ID NO:13:

GAACCACTCC GGGCCTATGC GGC                                                23

(2) INFORMATION FOR SEQ ID NO:14:

(i) SEQUENCE CHARACTERISTICS:
        (A) LENGTH: 25 base pairs
        (B) TYPE: nucleic acid
        (C) STRANDEDNESS: single
        (D) TOPOLOGY: linear (xi) SEQUENCE DESCRIPTION: SEQ ID NO:14:

GATCTCTGAG TTCGTCCTCA GCGAG                                              25

(2) INFORMATION FOR SEQ ID NO:15:

(i) SEQUENCE CHARACTERISTICS:
        (A) LENGTH: 24 base pairs
        (B) TYPE: nucleic acid
        (C) STRANDEDNESS: single
        (D) TOPOLOGY: linear (xi) SEQUENCE DESCRIPTION: SEQ ID NO:15:

CGACGGTTCC AGTGATTTTC ATGG                                               24

(2) INFORMATION FOR SEQ ID NO:16:

(i) SEQUENCE CHARACTERISTICS:
        (A) LENGTH: 21 base pairs
        (B) TYPE: nucleic acid
        (C) STRANDEDNESS: single
        (D) TOPOLOGY: linear (xi) SEQUENCE DESCRIPTION: SEQ ID NO:16:

CCGTATCTGC AGCGGGGGGT C                                                  21

(2) INFORMATION FOR SEQ ID NO:17:

(i) SEQUENCE CHARACTERISTICS:
        (A) LENGTH: 671 base pairs
        (B) TYPE: nucleic acid
        (C) STRANDEDNESS: single
        (D) TOPOLOGY: linear (xi) SEQUENCE DESCRIPTION: SEQ ID NO:17:

ACCTGATTCC GGCAAATGTG AACGCCGACA TCAAGGCGAC CACGGTGTTC GGCGGTAAGT         60

ATGTGTCGTT GACCACGCCG AAAAACCCGA CAAAGAGGCG CATAACGCCA AAAGACGTCA        120

TCGACGTACG GTCGGTGACC ACCGAGATCA ACACGTTGTT CCAGACGCTC ACCTCGATCG        180

CCGAGAAGGT GGATCCGGTC AAGCTGAACC TGACCCTGAG CGCGGCCGCG GAGGCGTTGA        240

CCGGGCTGGG CGATAAGTTC GGCGAGTCGA TCGTCAACGC CAACACCGTT CTGGATGACC        300

TCAATTCGCG GATGCCGCAG TCGCGCCACG ACATTCAGCA ATTGGCGGCT CTGGGCGACG        360

TCTACGCCGA CGCGGCGCCG GACCTGTTCG ACTTTCTCGA CAGTTCGGTG ACCACCGCCC        420

GCACCATCAA TGCCCAGCAA GCGGAACTGG ATTCGGCGCT GTTGGCGGCG GCCGGGTTCG        480

GCAACACCAC AGCCGATGTC TTCGACCGCG GCGGGCCGTA TCTGCAGCGG GGGTCGCCG         540

ACCTGGTCCC CACCGCCACC CTGCTCGACA CTTATAGCCC GGAACTGTTC TGCACGATCC        600

-continued

```
GCAACTTCTA CGATGCCGAT CGACCTGACC GCGGGGCTGC CGCATAGGCC CGGAGTGGTT      660

CGCGATCGGC G                                                           671
```